(12) United States Patent
Kedmi et al.

(10) Patent No.: US 11,338,042 B2
(45) Date of Patent: May 24, 2022

(54) IMMUNOPARTICLES AND METHODS OF GENERATING AND USING SAME

(71) Applicant: Ramot at Tel-Aviv University Ltd., Tel-Aviv (IL)

(72) Inventors: Ranit Kedmi, Tel-Aviv (IL); Dan Peer, Kiryat-Ono (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 379 days.

(21) Appl. No.: 16/701,184

(22) Filed: Dec. 3, 2019

(65) Prior Publication Data

US 2020/0101170 A1    Apr. 2, 2020

Related U.S. Application Data

(62) Division of application No. 14/427,711, filed as application No. PCT/IL2013/050775 on Sep. 12, 2013, now Pat. No. 10,543,278.

(30) Foreign Application Priority Data

Sep. 12, 2012   (IL) .......................................... 221909

(51) Int. Cl.

| A61K 39/395 | (2006.01) |
|---|---|
| A61K 47/68 | (2017.01) |
| C07K 16/28 | (2006.01) |
| C07K 16/42 | (2006.01) |
| B82Y 5/00 | (2011.01) |
| A61K 47/69 | (2017.01) |
| C07K 16/30 | (2006.01) |
| A61K 39/00 | (2006.01) |

(52) U.S. Cl.
CPC ...... *A61K 47/6809* (2017.08); *A61K 47/6849* (2017.08); *A61K 47/6851* (2017.08); *A61K 47/6897* (2017.08); *A61K 47/6909* (2017.08); *A61K 47/6921* (2017.08); *B82Y 5/00* (2013.01); *C07K 16/2809* (2013.01); *C07K 16/2812* (2013.01); *C07K 16/2839* (2013.01); *C07K 16/2896* (2013.01); *C07K 16/30* (2013.01); *C07K 16/4283* (2013.01); *A61K 2039/505* (2013.01); *C07K 2317/622* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| 5,530,101 A | 6/1996 | Queen et al. |
|---|---|---|
| 5,814,318 A | 9/1998 | Lonberg et al. |
| 6,440,736 B1 | 8/2002 | Logtenberg et al. |
| 7,575,871 B2 | 8/2009 | Griffin et al. |
| 7,611,866 B2 | 11/2009 | Georgiou et al. |
| 8,535,890 B2 | 9/2013 | Kashmiri et al. |
| 2004/0058403 A1 | 3/2004 | Harvey et al. |
| 2013/0064762 A1* | 3/2013 | Simon .............. G01N 33/57415 435/7.1 |
| 2015/0246135 A1 | 9/2015 | Kedmi et al. |
| 2019/0309087 A1 | 10/2019 | Kedmi et al. |

FOREIGN PATENT DOCUMENTS

| EP | 0506124 | 9/1992 |
|---|---|---|
| WO | WO 91/07987 | 6/1991 |
| WO | WO 99/01556 | 1/1999 |
| WO | WO 2005/060457 | 7/2005 |
| WO | WO 2006/078987 | 7/2006 |
| WO | WO 2006/082406 | 8/2006 |
| WO | WO 2007/127272 | 11/2007 |
| WO | WO 2008/116149 | 9/2008 |
| WO | WO 2011/139792 | 11/2011 |
| WO | WO 2014/041544 | 3/2014 |
| WO | WO 2018/015881 | 1/2018 |

OTHER PUBLICATIONS

Applicant-Initiated Interview Summary dated Apr. 12, 2018 From the US Patent and Trademark Office Re. U.S. Appl. No. 14/427,711. (3 pages).
Communication Pursuant to Article 94(3) EPC dated May 29, 2019 From the European Patent Office Re. Application No. 13779639.7. (4 Pages).
International Preliminary Report on Patentability dated Mar. 26, 2015 From the International Bureau of WIPO Re. Application No. PCT/IL2013/050775.
International Preliminary Report on Patentability dated Jan. 31, 2019 From the International Bureau of WIPO Re. Application No. PCT/IB2017/054334. (11 Pages).
International Search Report and the Written Opinion dated Nov. 8, 2017 From the International Searching Authority Re. Application No. PCT/IB2017/054334. (15 Pages).
International Search Report and the Written Opinion dated Feb. 21, 2014 From the International Searching Authority Re. Application No. PCT/IL2013/050775.
Office Action and Search Report dated Mar. 17, 2013 From the Israel Patent Office Re. Application No. 221909.
Official Action dated Feb. 8, 2018 From the US Patent and Trademark Office Re. U.S. Appl. No. 14/427,711. (11 pages).
Official Action dated Mar. 18, 2019 From the US Patent and Trademark Office Re. U.S. Appl. No. 14/427,711. (7 pages).

(Continued)

*Primary Examiner* — Meera Natarajan

(57) ABSTRACT

A pharmaceutical composition comprising an immunoparticle is provided. The pharmaceutical composition comprising a monoclonal secondary antibody immunocomplexed with a primary antibody, wherein said monoclonal secondary antibody is coupled on an outer surface of a particle and wherein said particle is loaded with a pharmaceutical agent.

11 Claims, 12 Drawing Sheets

(11 of 12 Drawing Sheet(s) Filed in Color)

(56) References Cited

OTHER PUBLICATIONS

Official Action dated Jul. 19, 2017 From the US Patent and Trademark Office Re. U.S. Appl. No. 14/427,711. (10 pages).
Official Action dated Sep. 20, 2018 From the US Patent and Trademark Office Re. U.S. Appl. No. 14/427,711. (10 pages).
Official Action dated Dec. 30, 2016 From the US Patent and Trademark Office Re. U.S. Appl. No. 14/427,711. (14 pages).
Restriction Official Action dated Sep. 9, 2016 From the US Patent and Trademark Office Re. U.S. Appl. No. 14/427,711.
Restriction Official Action dated Oct. 30, 2019 From the US Patent and Trademark Office Re. U.S. Appl. No. 16/316,629. (6 Pages).
Ansell et al. "Antibody Conjugation Methods for Active Targeting of Liposomes", Methods in Molecular Medicine: Drug Targeting: Strategies, Principles, and Applications, 25(Chap.4): 51-67, 2000.
Begent et al. "Liposomally Entrapped Second Antibody Improves Tumour Imaging With Radiolabelled (First) Antitumour Antibody", The Lancet, XP055101004, p. 739-742, Oct. 2, 1982.
Braisted et al. "Minimizing A Binding Domain From Protein A", Proc. Natl. Acad. Sci. USA, 93(12): 5688-5692, Jun. 11, 1996.
Choe et al. "Fc-Binding Ligands of Immunoglobulin G: An Overview of High Affinity Proteins and Peptides", Materials, 9(12): 994-1-994-17, Dec. 8, 2016.
De Kruif et al. "Biosynthetically Lipid-Modified Human ScFv Fragments From Phage Display Libraries as Targeting Molecules for Immunoliposomes", FEBS Letters, 399(3): 232-236, Dec. 16, 1996.
Harvey et al. "Anchored Periplasmic Expression, A Versatile Technology for the Isolation of High-Affinity Antibodies From *Escherichia coli*-Expressed Libraries", Proc. Natl. Acad. Sci. USA, PNAS, 101(25): 9193-9198, Jun. 22, 2004. Fig. 1.
Jeong et al. "Efficiant Selection of IgG Fc Domain-Binding Peptides Fused to Fluorescent Protein Using *E. coli* Expression System and Dot-Blotting Assay", Peptides, 31(2): 202-206, Available Online Dec. 16, 2009.
Jones et al. "Blood-Brain Barrier Transport of Therapeutics Via Receptor-Mediation", Pharmaceutical Research. XP019532601, 24(9): 1759-1771, Jul. 10, 2007. Abstract, p. 1767-1769.
Julien et al. "Utilization of Monoclonal Antibody-Targeted Nanomaterials in the Treatment of Cancer", MAbs, 3(5): 467-478, Sep./Oct. 2011.
Krystofiak et al. "Elimination of Tumor Cells U sing Folate Receptor Targeing by Antibody-Conjugated, Gold-Coated Magnetite Nanoparticles in A Murine Breast Cancer Model", Journal of Nanomaterials, 2012: Article ID 431012, 9 P., 2012.
Laukkanen et al. "Lipid-Tagged Antibodies: Bacterial Expression and Characterization of A Lipoprotein—Single-Chain Antibody Fusion Protein", Protein Engineering, 6(4): 449-454, 1993.
Leserman et al. "Targeting to Cells of Fluorescent Liposomes Covalently Coupled With Monoclonal Antibody or Protein A", Nature, 288: 602-604, Dec. 11, 1980.
Li et al. "Electrochemical Immunosensors for Cancer Biomarker With Signal Amplification Based on Ferrocene Functionalized Iron Oxide Nanoparticles", Biosensors and Bioelectronics, XP028369905, 26(8): 3590-3595, Feb. 4, 2011. Abstract.
Matthay et al. "Antibody-Directed Liposomes: Comparison of Various Ligands for Association, Endocytosis, and Drug Delivery", Cancer Research, 46: 4904-4910, Oct. 1986.
Owens "Faster, Deeper, Smaller—The Rise of Antibody-Like Scaffolds", Nature Biotechnology, 35(7): 602-603, Jul. 2017.
Pitsillides et al. "Selctive Cell Targeting With Light-Absorbing Microparticles and Nanoparticles", Biophysical Journal, XP002428862, 84(6): 4023-4032, Jun. 1, 2003. p. 4028.
Presta et al. "Humanization of An Antibody Directed Against IgE", The Journal of Immunology, XP002094432. 151(5): 2623-2632, Sep. 1, 1993. Abstract. p. 2624, 2629-2631.
Ritter et al. "Serological Analysis of Human Anti-Hun:1an Antibody Responses in Colon Cancer Patients Treated with Repeated Doses of Humanized 1 Vlonodonal Antibody A33", Cancer Research 61:6851-6859, Sep. 15, 2001.
Serda et al. "Quantitative Mechanics of Endothelial Phagocytosis of Silicon Microparticles", Cytometry Part A, XP008111439, 75(9): 752-760, Sep. 1, 2009. p. 757, r-h Col.
Torchilin "Fluorescence Microscopy to Follow the Targetin of Liposomes and Micelles to Cells and Their Intracellular Fate", Advanced Drug Delivery Reviews, XP027771274, 57(1): 95-109, Jan. 2, 2005. Abstract, p. 96, Line 97.
Torchilin et al. "P-Nitrophenylcarbonyl-PEG-PE-Liposomes: Fast and Simple Attachment of Specific Ligands, Including Monoclonal Antibodies, to Distal Ends of PEG Chains Via P-Nitrophenylcarbonyl Groups", Biochimica et Biophysica Acta, XP002257432, 1511(2): 397-411, Apr. 2 p. 404.
Ugelstad et al. "Biomedical Applications of Monodisperse Magnetic Polymer Particles", Nato Advanced Science Institute, XP000603237, p. 355-370, Jan. 1, 1987. p. 361.
Van der Heyde et al. "Analysis of Antigen-Specific Antibodies and Their Isotypes in Experimental Malaria", Cytometry Part A, The Journal of the International Society for Analytical Cytology, 71(4): 242-250, 2007.
Vazquez-Lombardi et al. "Challenges and Opportunities for Non-Antibody Scaffold Drugs", Drug Discovery Today, 20(10): 1271-1283, Oct. 2015.
Wu et al. "Immunofluorescence Labeling of Cancer Marker Her2 and Other Cellular Targets With Semiconductor Quantum Dots", Nature Biotechnology, 21: 41-46, Jan. 2003.
Official Action dated Mar. 9, 2020 From the US Patent and Trademark Office Re. U.S. Appl. No. 16/316,629. (25 pages).
Supplementary European Search Report and the European Search Opinion dated Mar. 12, 2020 From the European Patent Office Re. Application No. 17830577.7. (9 Pages).
Ben-Arie et al. "Integrin-Targeted Nanoparticles for siRNA Delivery", Integrin and Cell Adhesion Molecules: Methods and Protocols, Methods in Molecular Biology, XP055136709, 757(Chap.29): 497-507, Published Online Jun. 8, 2011.
Delgoffe et al. "Enhanced Interaction Between Hsp90 and Raptor Regulates mTOR Signaling Upon T Cell Activation", Molecular immunology, 46(13): 2694-2698, Aug. 1, 2009.
Kedmi et al. "A Modular Platform for Targeted RNAi Therapeutics", Nature Nanotechnology, XP036449126, 13(3): 214-219, Published Online Jan. 29, 2018.
Official Action dated Mar. 23, 2021 from the US Patent and Trademark Office Re. U.S. Appl. No. 16/316,629. (9 pages).
Advisory Action dated Nov. 9, 2021 From the US Patent and Trademark Office Re. U.S. Appl. No. 16/316,629. (3 Pages).
Final Official Action dated Aug. 25, 2020 from the US Patent and Trademark Office Re. U.S. Appl. No. 16/316,629. (16 pages).
Official Action dated Dec. 24, 2021 from US Patent and Trademark Office Re. U.S. Appl. No. 16/316,629. (12 pages).
Kruif et al. "Bio synthetically Lipid-Modified Human scFv Fragments From Phage Display Libraries as Targeting Molecules for Immunoliposomes", FEBS Letters, 399(3): 232-236. Dec. 16, 1996.

* cited by examiner

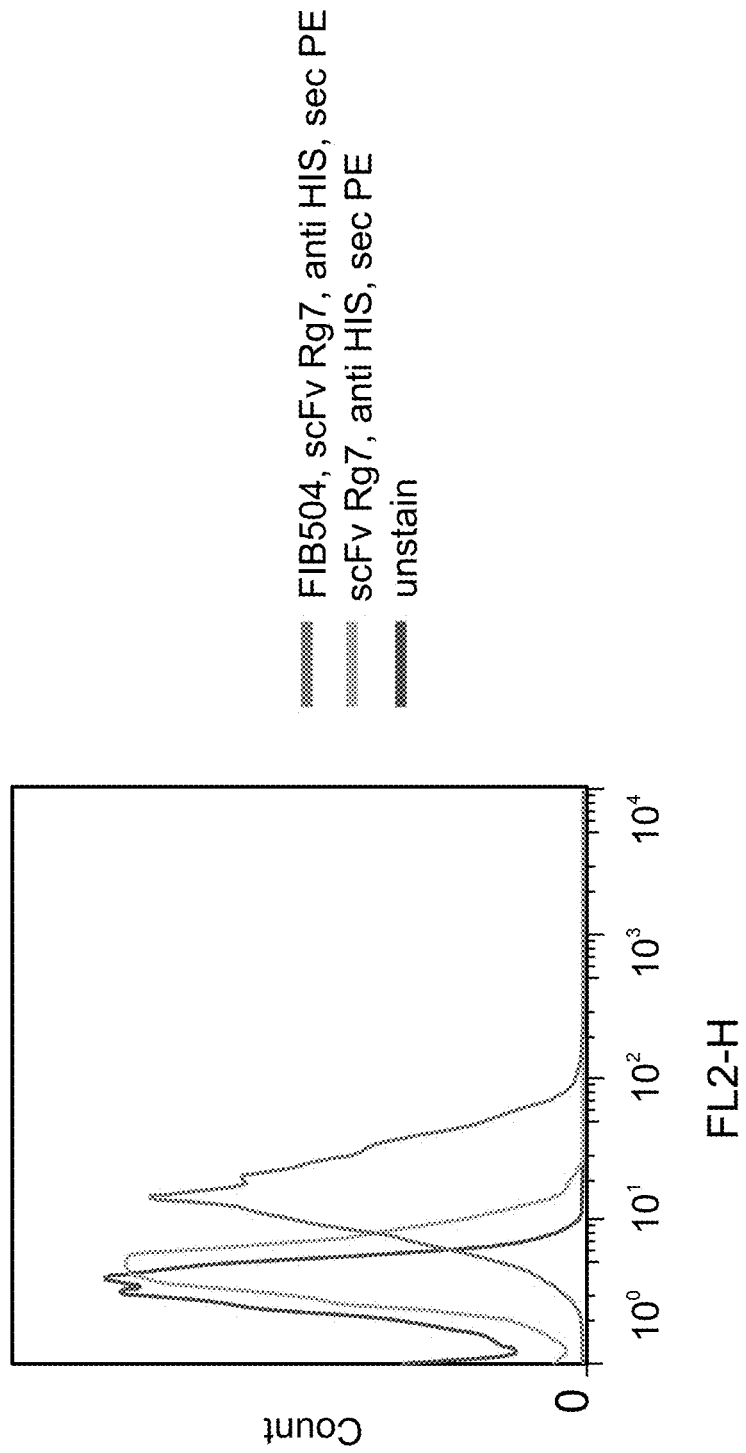

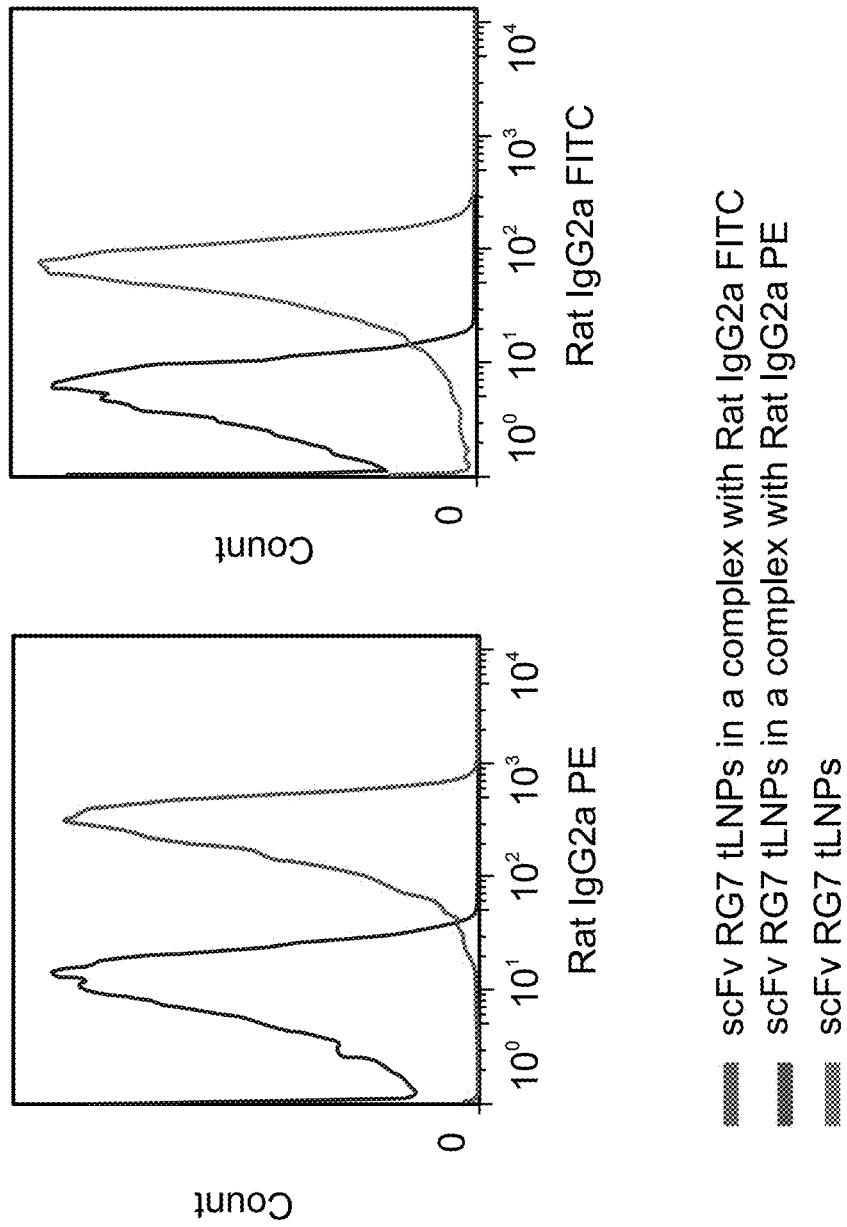

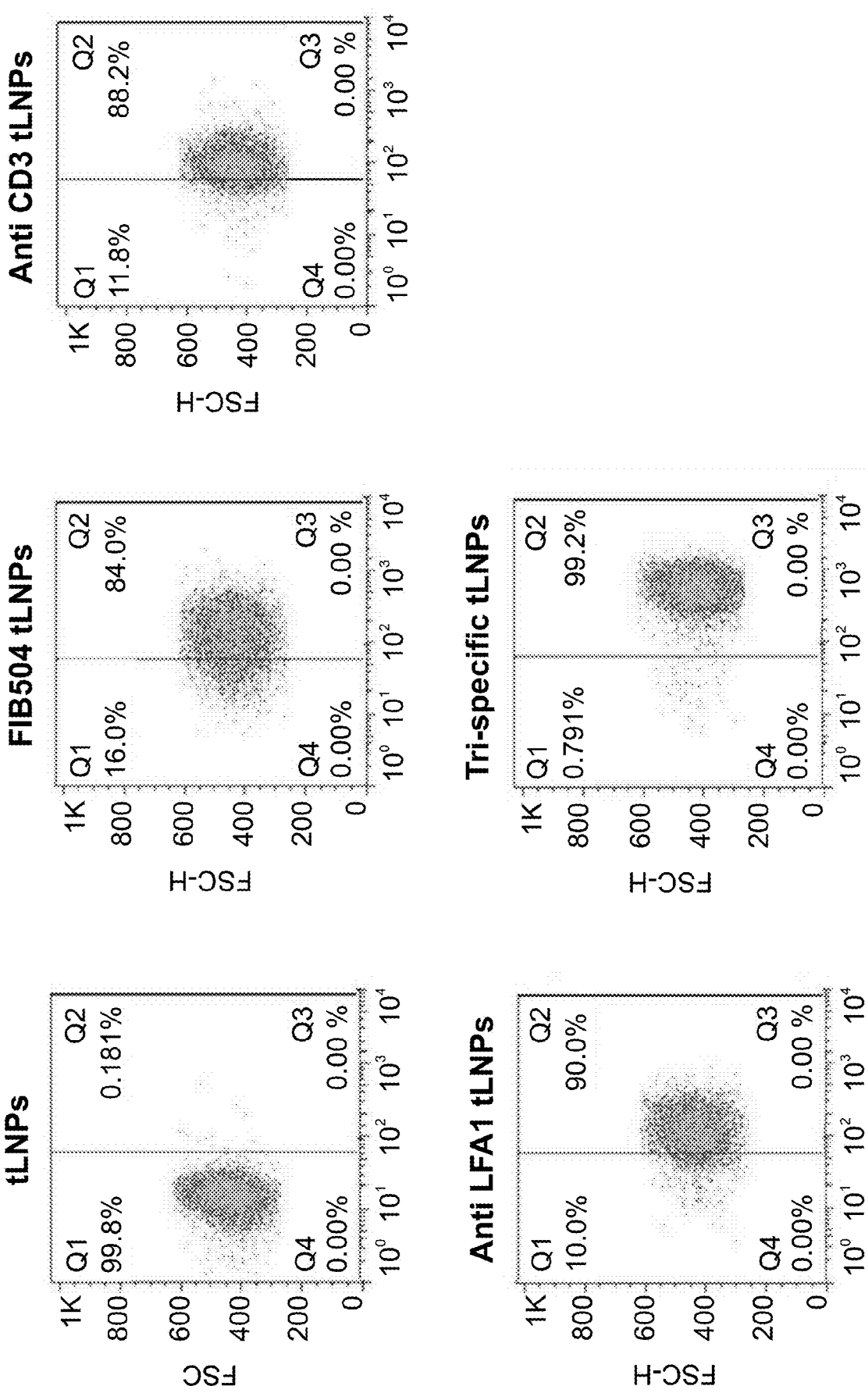

IMMUNOPARTICLES AND METHODS OF GENERATING AND USING SAME

RELATED APPLICATIONS

This application is a division of U.S. patent application Ser. No. 14/427,711 filed on Mar. 12, 2015, which is a National Phase of PCT Patent Application No. PCT/IL2013/050775 having International Filing Fate of Sep. 12, 2013, which claims the benefit of priority of Israel Patent Application No. 221909 filed on Sep. 12, 2012. The contents of the above applications are all incorporated by reference as if fully set forth herein in their entirety.

FIELD AND BACKGROUND OF THE INVENTION

The present invention, in some embodiments thereof, relates to immunoparticles and methods of generating and using same.

Liposomes are useful drug delivery vehicles since they may protect encapsulated drugs from enzymatic degradation and rapid clearance in vivo, or alter biodistribution, potentially leading to reduced toxicities. A major limitation to the development of many specialized applications is the problem of directing liposomes to tissues where they would not normally accumulate. Consequently a great deal of effort has been made over the years to develop liposomes that have targeting moieties attached to their surface. These targeting moieties have included ligands, such as oligosaccharides, peptides, proteins and vitamins. Most studies have focused on antibody conjugation since procedures for producing monoclonal antibodies against a tissue target of interest are well established.

Numerous procedures for the conjugation of antibodies to liposomes have been developed. These fall into four general categories defined by the particular functionality of the antibody being modified, namely amine modification, carbohydrate modification, disulfide modification and non-covalent conjugation. However most of these approaches result in loss of antibody variable region structure which results in loss of binding activity. In addition, current procedures for generating immunoliposomes are inefficient resulting in loss of precious amounts of antibody.

Indirect methods for generating immunoliposomes using receptor-ligand-like systems are known. For, example, liposome avidin conjugates have been shown to effectively target biotinylated antibodies to known cell/tissue surface antigens. However, such an approach requires both modifications of the antibody (e.g., biotinylation) and the liposomes (avidin), which again may hamper antibody functionality.

A similar approach has frequently been used with protein A/G-liposome conjugates targeted to the Fc chain of antibodies. This approach, is not suitable for in vivo applications because of competition from the general IgG population.

Review of the field is available by Ansell et al. Methods in Molecular Medicine, Vol 25: Drug Targeting: Strategies, Principles and Applications Edited by: G. E. Francis and C. Delgado© Humana Press, Inc., ToTowa, N.J.

Leserman et al. 1980 Nature 288:602-604 teaches targeting of fluorescent liposomes covalently coupled with monoclonal antibody or protein A to cells precoated with an antibody. Like protein A/G this approach, is not suitable for in vivo applications because of competition from the general IgG population.

Additional Related Art

1. Krystofiak et al. (2012) J. Nanomaterials Volume 2012, Article ID 431012;
2. Wo et al. 2002 Natura Biotechnology 21:41-46;
3. WO 2011139792;
4. Julien et al. 2011 mAbs 3(5):467-478;

SUMMARY OF THE INVENTION

According to an aspect of some embodiments of the present invention there is provided a pharmaceutical composition comprising an immunoparticle comprising a monoclonal secondary antibody immunocomplexed with a primary antibody, wherein the monoclonal secondary antibody is coupled on an outer surface of a particle and wherein the particle is loaded with a pharmaceutical agent.

According to some embodiments of the invention, the monoclonal secondary antibody is a humanized monoclonal secondary antibody.

According to an aspect of some embodiments of the present invention there is provided a method of delivering a pharmaceutical agent to a subject in need thereof, the method comprising administering to the subject the pharmaceutical, thereby delivering the pharmaceutical agent to the subject.

According to an aspect of some embodiments of the present invention there is provided an isolated humanized secondary antibody.

According to some embodiments of the invention, the secondary antibody is a monoclonal antibody.

According to some embodiments of the invention, the secondary antibody comprising an antigen recognition domain capable of specifically binding a humanized or human primary antibody.

According to an aspect of some embodiments of the present invention there is provided an immunoparticle comprising the secondary antibody coupled on an outer surface of a particle.

According to some embodiments of the invention, the secondary antibody is immunocomplexed with a humanized or human primary antibody.

According to an aspect of some embodiments of the present invention there is provided an immunoparticle comprising a humanized secondary antibody coupled on an outer surface of a particle, wherein the secondary antibody is immunocomplexed with a humanized or human primary antibody.

According to some embodiments of the invention, the immunoparticle is loaded with a pharmaceutical agent.

According to an aspect of some embodiments of the present invention there is provided a pharmaceutical composition comprising the humanized secondary antibody or the immunoparticle.

According to an aspect of some embodiments of the present invention there is provided a universal kit for in-vivo delivery of a pharmaceutical agent, the kit comprising the immunoparticle and instructions for effecting immunocomplexation of the secondary antibody to a primary antibody.

According to an aspect of some embodiments of the present invention there is provided a universal kit for in-vivo delivery of a pharmaceutical agent, the kit comprising, an immunoparticle comprising a monoclonal secondary antibody coupled on an outer surface of a lipid-based particle, and instructions for effecting immunocomplexation of the secondary antibody to a primary antibody.

According to some embodiments of the invention, the pharmaceutical agent is a diagnostic agent.

According to some embodiments of the invention, the pharmaceutical agent is a therapeutic agent.

According to some embodiments of the invention, the monoclonal secondary antibody being coupled on an outer surface of the particle is coupled to the outer surface not via the primary antibody.

According to an aspect of some embodiments of the present invention there is provided a method of generating an immunoparticle, the method comprising incubating the humanized secondary antibody with a particle under conditions which result in an immunoparticle having coupled on an outer surface thereof a the humanized secondary antibody.

According to some embodiments of the invention, the conditions comprise amine-coupling reaction.

According to some embodiments of the invention, the conditions result in directional coupling of the secondary antibody to the outer surface of the particle, such that the secondary antibody maintains its functionality following the coupling.

According to some embodiments of the invention, the method further comprises incubating the immunoparticle with a primary antibody under conditions which allow immunocomplexation of the secondary antibody with the primary antibody.

According to some embodiments of the invention, the incubating the immunoparticle with a primary antibody is effected ex-vivo.

According to some embodiments of the invention, the administering is systemically administering.

According to some embodiments of the invention, the primary antibody comprises an Fc region.

According to some embodiments of the invention, the secondary antibody is an antibody fragment and optionally wherein the fragment is selected from the group consisting of a Fab, F(ab)$_2$ an ScFv and a sdFv.

According to some embodiments of the invention, the primary antibody and the secondary antibody are of different antibody classes or antibody isotypes.

According to some embodiments of the invention, the primary antibody and the secondary antibody are selected from the group consisting of IgG1, IgG2 and IgG4.

According to some embodiments of the invention, the primary antibody is an IgG1 and the secondary antibody is an IgG2 or IgG4.

According to some embodiments of the invention, the primary antibody comprises a plurality of primary antibodies which bind distinct targets.

According to some embodiments of the invention, the primary antibody is selected from the group consisting of anti-CD3, anti-LFA-1, anti-integrin beta 7, and anti-CD4.

According to some embodiments of the invention, the primary antibody comprises an antigen recognition region which binds a tissue specific antigen.

According to some embodiments of the invention, the primary antibody comprises an antigen recognition region which binds a cancer specific antigen.

According to some embodiments of the invention, the particle is selected from the group consisting of a polymeric particle, a microcapsule, a liposome, a microsphere, a microemulsion, a nanoparticle, a nanocapsule, a nanosphere and a nanocage.

According to some embodiments of the invention, the particle comprises a charged external surface.

According to some embodiments of the invention, the particle comprises a neutral external surface.

According to some embodiments of the invention, the particle is lipid-based particle.

According to some embodiments of the invention, the lipids of the lipid based particle comprise cationic lipids.

According to some embodiments of the invention, the cationic lipid is selected from the group consisting of 1,2-Dilauroyl-sn-Glicero-3-Phosphoethanolamine (DLPE) and 1,2-Dilauroyl-sn-Glicero-3-Glycerol (DLPG), dioleoyl-1-diacyl-3-trimethylammonium-propane (DOTAP, at 18:1; 14:0; 16:0, 18:0) and N-[1-(2,3-dioleyloxy)propyl]-N,N,N-trimethylammonium chloride (DOTMA); dimethyldioctadecylammonium (DDAB); 1,2-dilauroyl-sn-glycero-3-ethylphosphocholine (Ethyl PC, at 12:0; 14:0; 16:0; 18:0; 18:1; 16:0-18:1); 1,2-di-(9Z-octadecenoyl)-3-dimethylammonium-propane and 3β-[N—(N',N'-dimethylaminoethane)-carbamoyl]cholesterol hydrochloride (DC-Cholesterol).

According to some embodiments of the invention, the lipids comprise a neutral lipid.

According to some embodiments of the invention, the neutral lipid comprises phosphatidylethanolamine or dioleilphosphatidylethanolamine (DOPE).

According to some embodiments of the invention, the lipids comprise anionic phospholipids.

According to some embodiments of the invention, the anionic phospholipids are selected from the group consisting of phosphatidylserine, phosphatidic acid, phosphatidylcholine and phosphatidyl glycerol.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
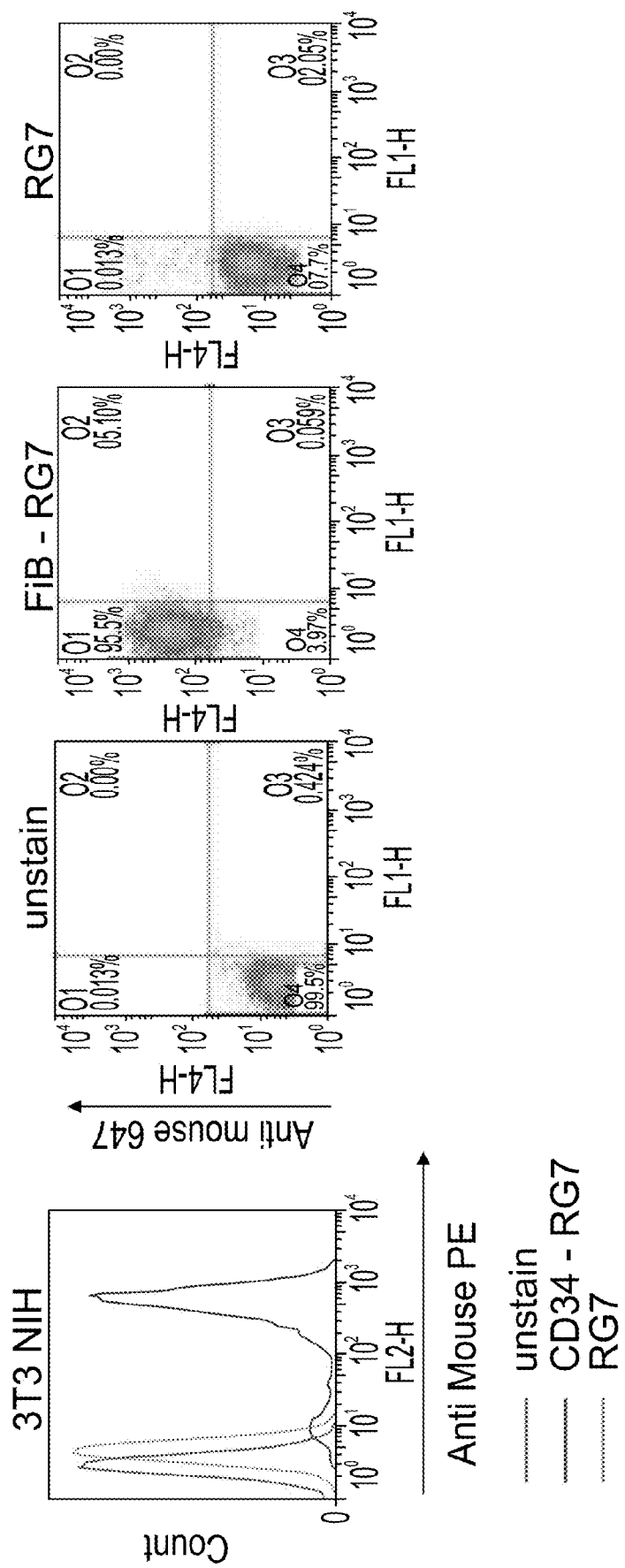

FIGS. 1A-1B are graphs showing binding of RG7 to Rat IgG2a. Rg7 was incubated with mec14.7 (FIG. 1A) and FIB504.64 (FIG. 1B) and bound to 3T3 NIH (FIG. 1A) and tk1 (FIG. 1B) cell lines respectively. As a control, RG7 was bound to cells without mec14.7 or FIB504.64. Detection was done using anti mouse PE (minimal cross to rat).

Figure 2:
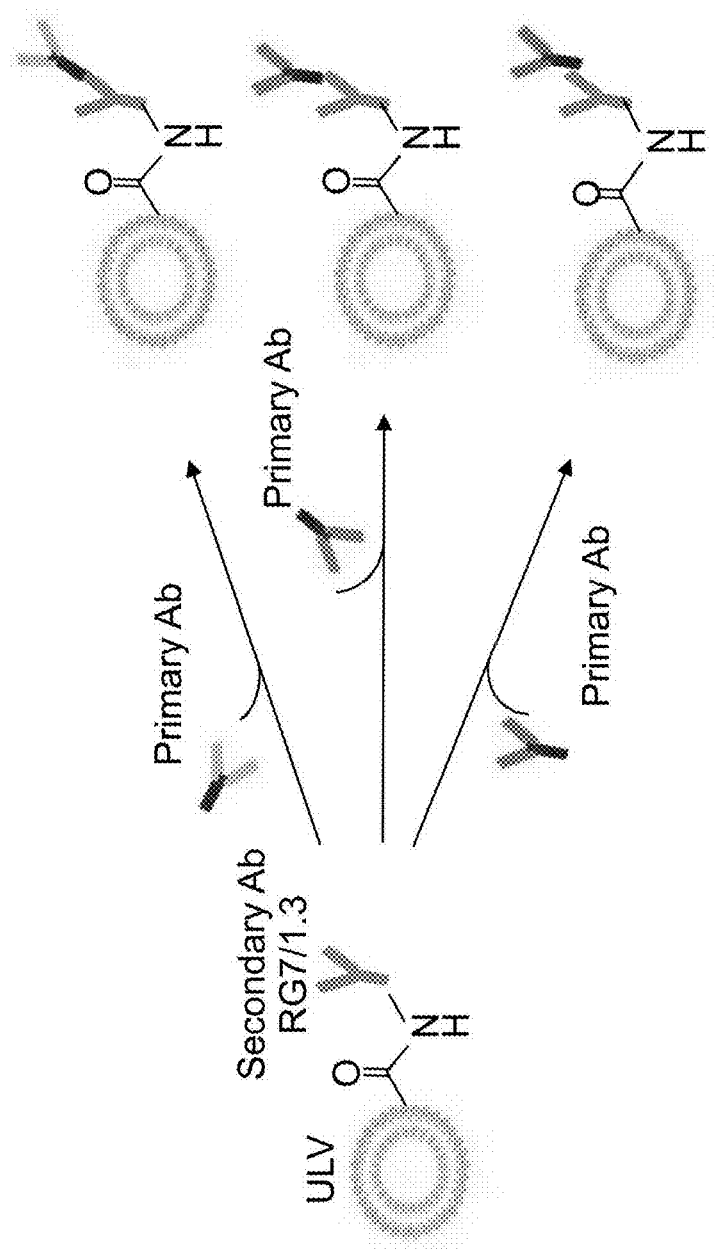

FIG. 2 is a schematic illustration of the design of universal LNPs (lipid-based nanoparticles (also referred to as tINPs).

LNPs conjugated to RG7 are incubated with exchangeable primary antibodies (from the Rat IgG$_{2a}$ isoclass) to assemble a delivery complex.

Figure 3A:
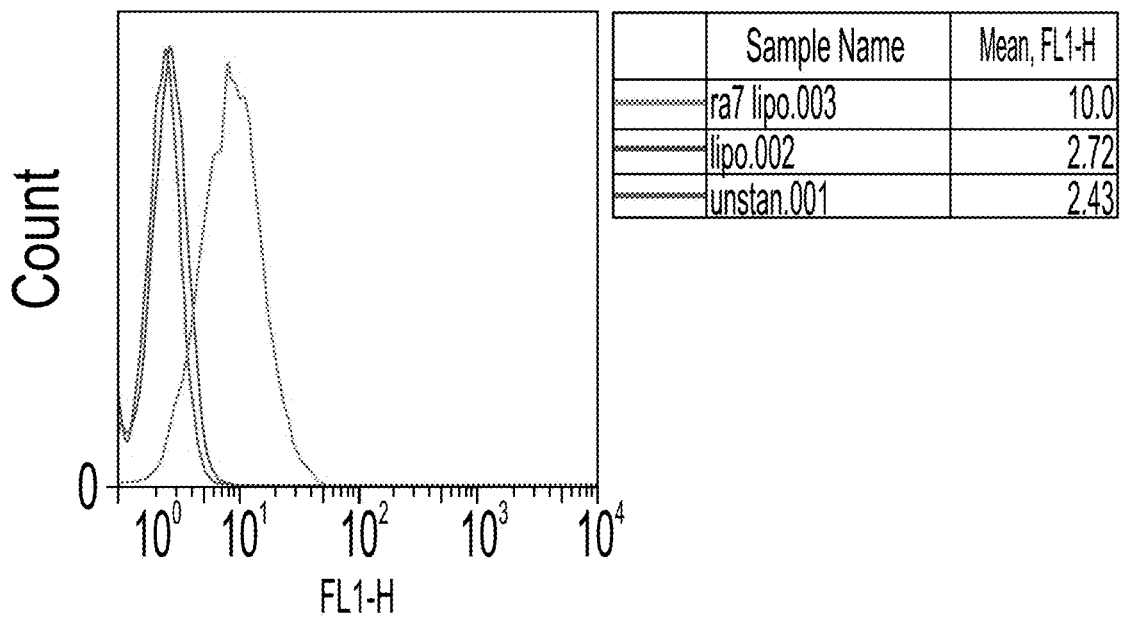
Figure 3B:
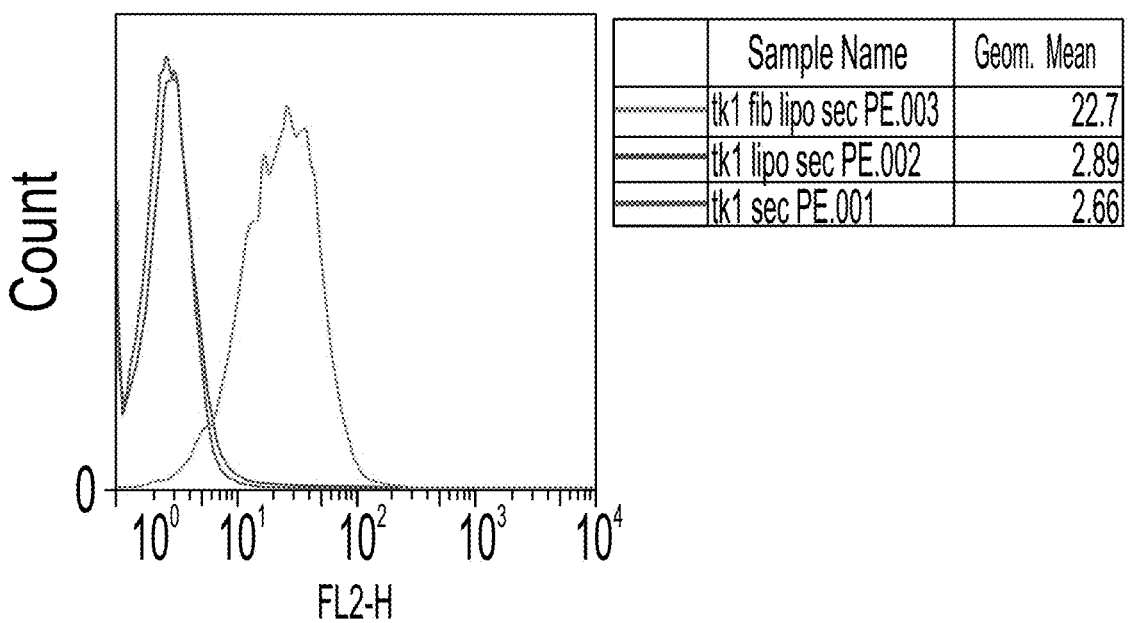

FIGS. 3A-3B are graphs substantiating the functionality of LNPs. Secondary LNPs bind specifically cells, previously bound to Rat IgG$_{2a}$ isoclass antibody. Tk1 cells were incubated with or without FIB504.64 and then were bound to secondary LNPs. Secondary LNPs were detected in the FL1 channel, due to the FITC dextran (FIG. 3A) or in the FL2 channel (FIG. 3B), using anti mouse PE (minimal cross to rat) that was bound specifically to RG7 antibody.

Figure 4A:
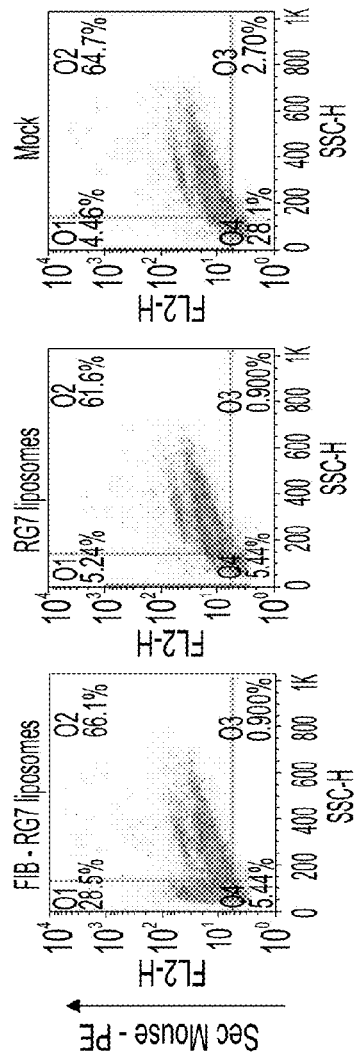
Figure 4B:
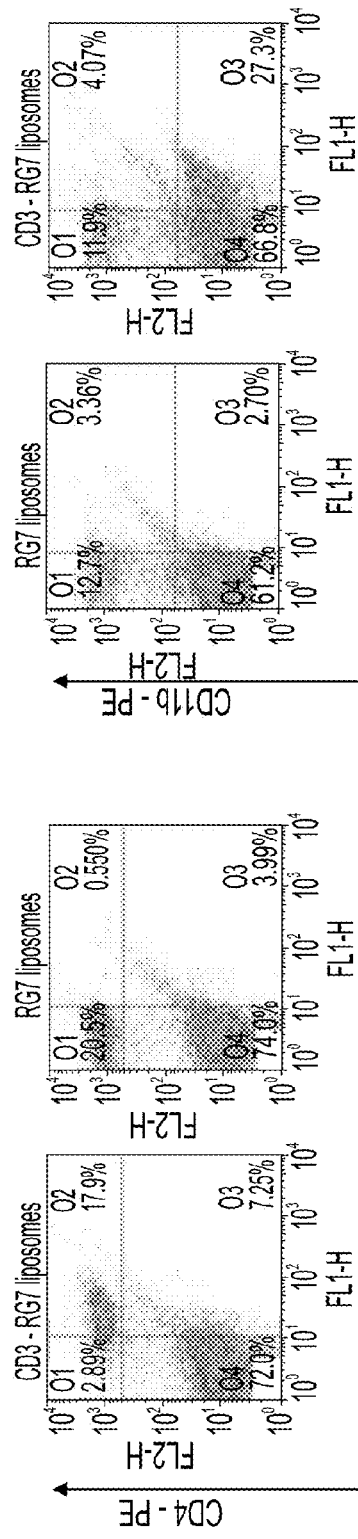
Figure 4C:
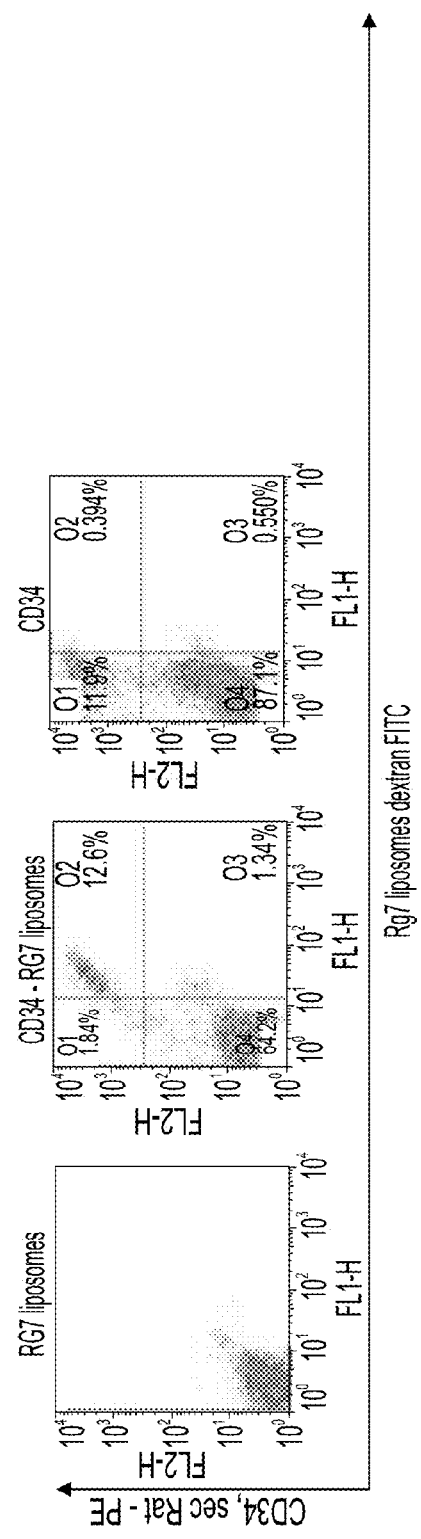

FIGS. 4A-4C are graphs showing that secondary LNPs can target a chosen cell type in a heterogeneous cell population. (FIG. 4A) Tk1 cells were co-culture with 3T3NIH cell line and incubated with or without FIB504.64 and then were bound to secondary LNPs. Secondary LNPs were detected in the FL2 channel, using anti mouse PE (minimal cross to rat) that was bound specifically to RG7 antibody. (FIG. 4B) Primary isolated splenocytes incubated with or without anti CD3 (Rat IgG$_{2a}$ isoclass) and then were bound to secondary LNPs. Secondary LNPs were detected in the FL1 channel, due to the FITC dextran encapsulation. To validate specification, splenocytes were stain with either anti CD4 PE (to stain T cells) or anti CD11b PE (to stain monocytes). (FIG. 4C) Primary isolated keratinocytes were incubated with anti CD34 PE (Rat IgG$_{2a}$ isoclass) and then were bound to secondary LNPs. Secondary LNPs were detected in the FL1 channel, due to the FITC dextran encapsulation.

Figure 5A:
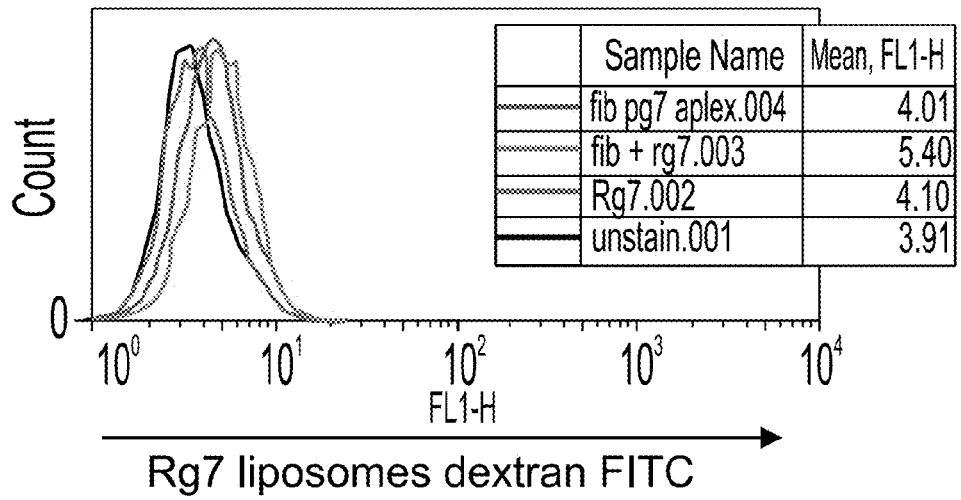
Figure 5B:
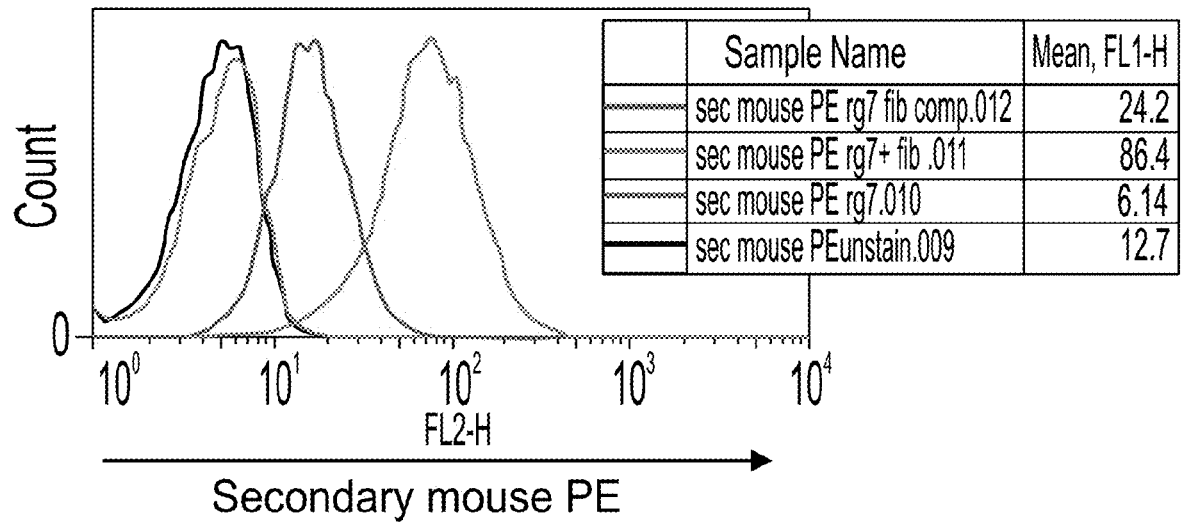
Figure 5C:
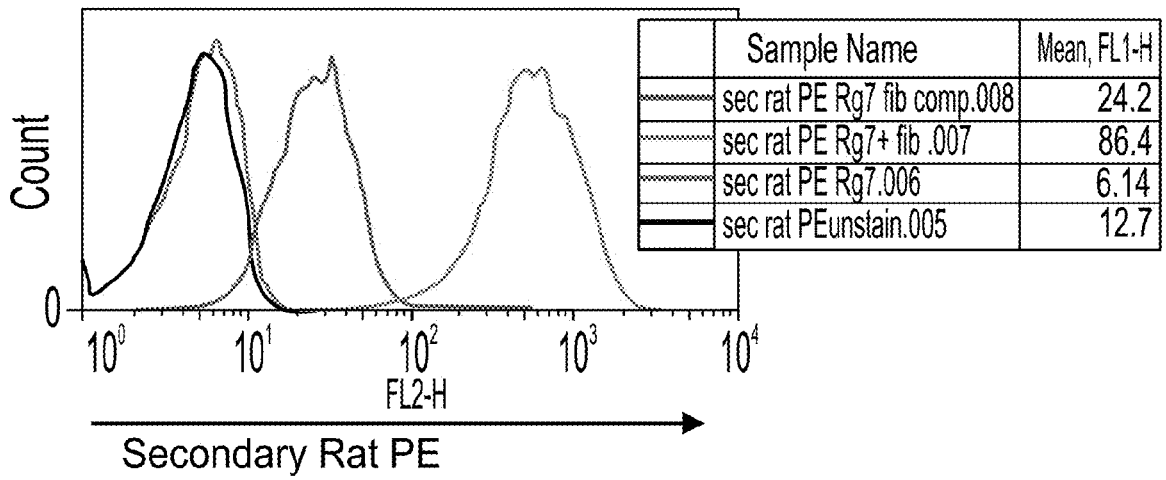

FIGS. 5A-5C are graphs showing that secondary LNPs—primary antibody complex can form and is functional. (FIG. 5A) Tk1 cells were incubated with secondary LNPs—FIB504.64 complex, secondary LNPs only or with FIB504.64 followed with secondary LNPs. (FIG. 5A) Secondary LNPs were detected in the FL1 channel, due to the FITC dextran. (FIG. 5B) Secondary LNPs were detected in the FL2 channel, using anti mouse PE (minimal cross to rat) that was bound specifically to RG7 antibody. (FIG. 5C) FIB504.64 was detected in the FL2 channel, using anti Rat PE (minimal cross to mouse).

Figure 6A:
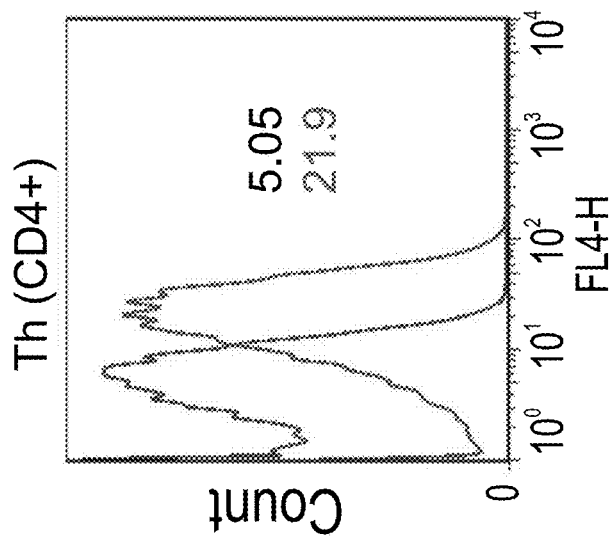
Figure 6B:
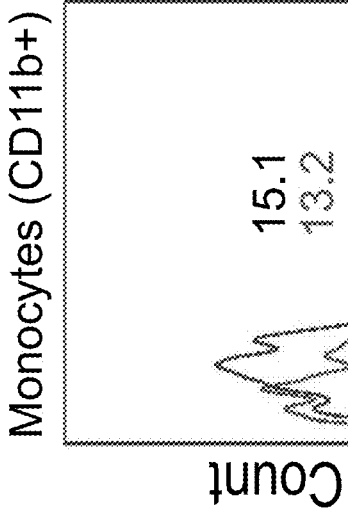
Figure 6C:
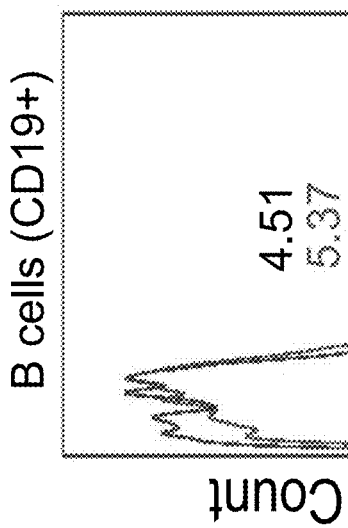

FIGS. 6A-6C are graphs showing the targeting of Secondary LNPs—primary antibody complex in-vivo. 20 mg/kg body of a secondary cy5 labeled LNPs antiCD3 complex were injected I.V to C57BL/6 mouse. An untreated mouse served as a control. One hour after injection, splenocytes were isolated and stained with CD4 PE, CD11b PE and CD19 PE to label T cells, monocytes and B cells respectively.

Figure 7A:
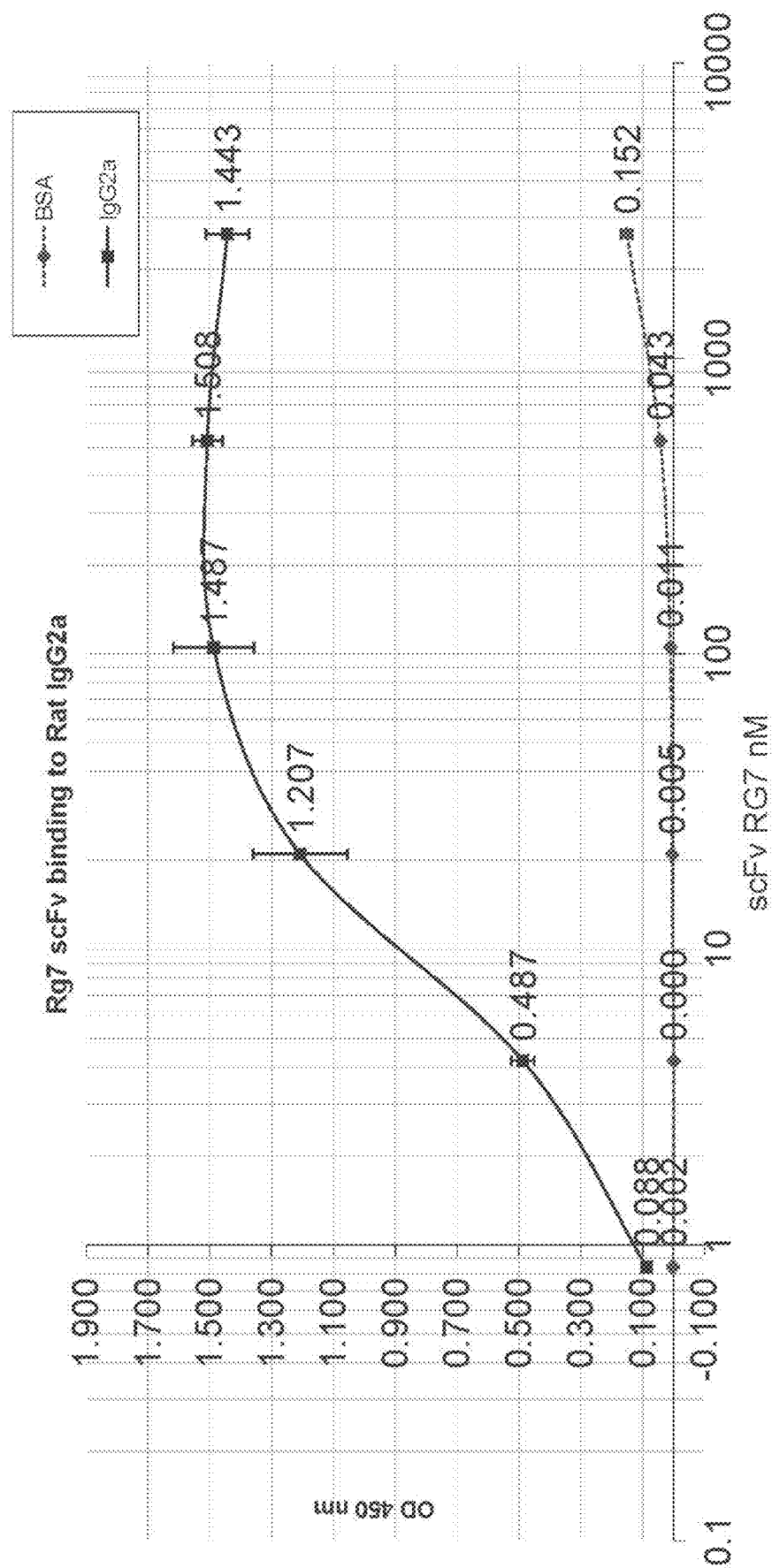
Figure 7D:
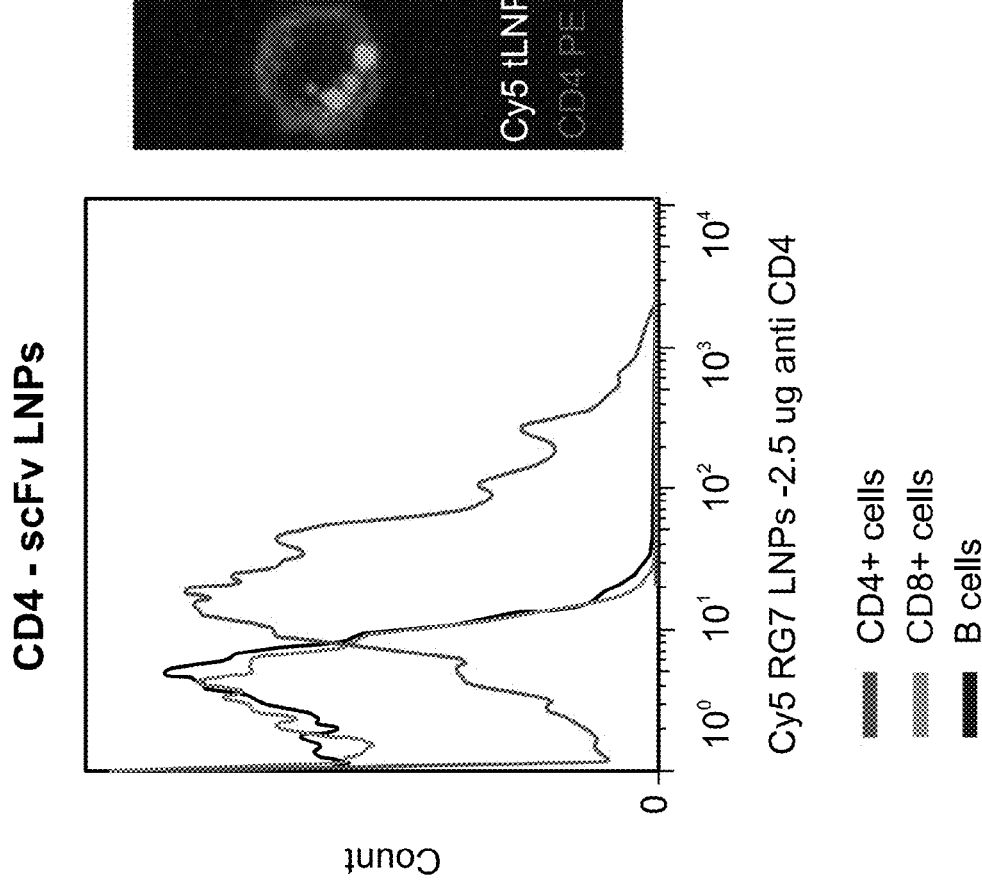

FIGS. 7A-7D show that scFv can be used as a secondary functional linker, specifically the scFv RG7 LNPs are functional and can be targeted In-Vivo: FIG. 7A is an ELISA assay of binding of the scFv RG7 to Rat IgG$_{2a}$ and not to BSA. FIG. 7B is a FACS analysis showing binding of scFv to Tk1 cells pre incubated with FIB504. To detect the scFv an anti HIS antibody was used, followed by anti mouse PE. FIG. 7C is a FACS analysis presenting LNPs fluorescence after incubation with FITC rat IgG$_{2a}$ or PE Rat IgG$_{2a}$. Free Rat IgG$_{2a}$ was removed using C14b column. FIG. 7D shows FACS and Confocal analyses presenting specific targeting to splenocytes of Cy5 CD4 scFv LNPs only to CD4+ population, but not to CD8+ or B cells after 1 hour.

FIG. 8 is a graphic presentation showing binding of secondary LNPs to multiple targets. RG7 LNPs were assembled with FIB504.64, anti-CD3, anti-LFA-1 or all the three. Binding to Tk1 cell line was tested by flow cytometry.

Figure 9:
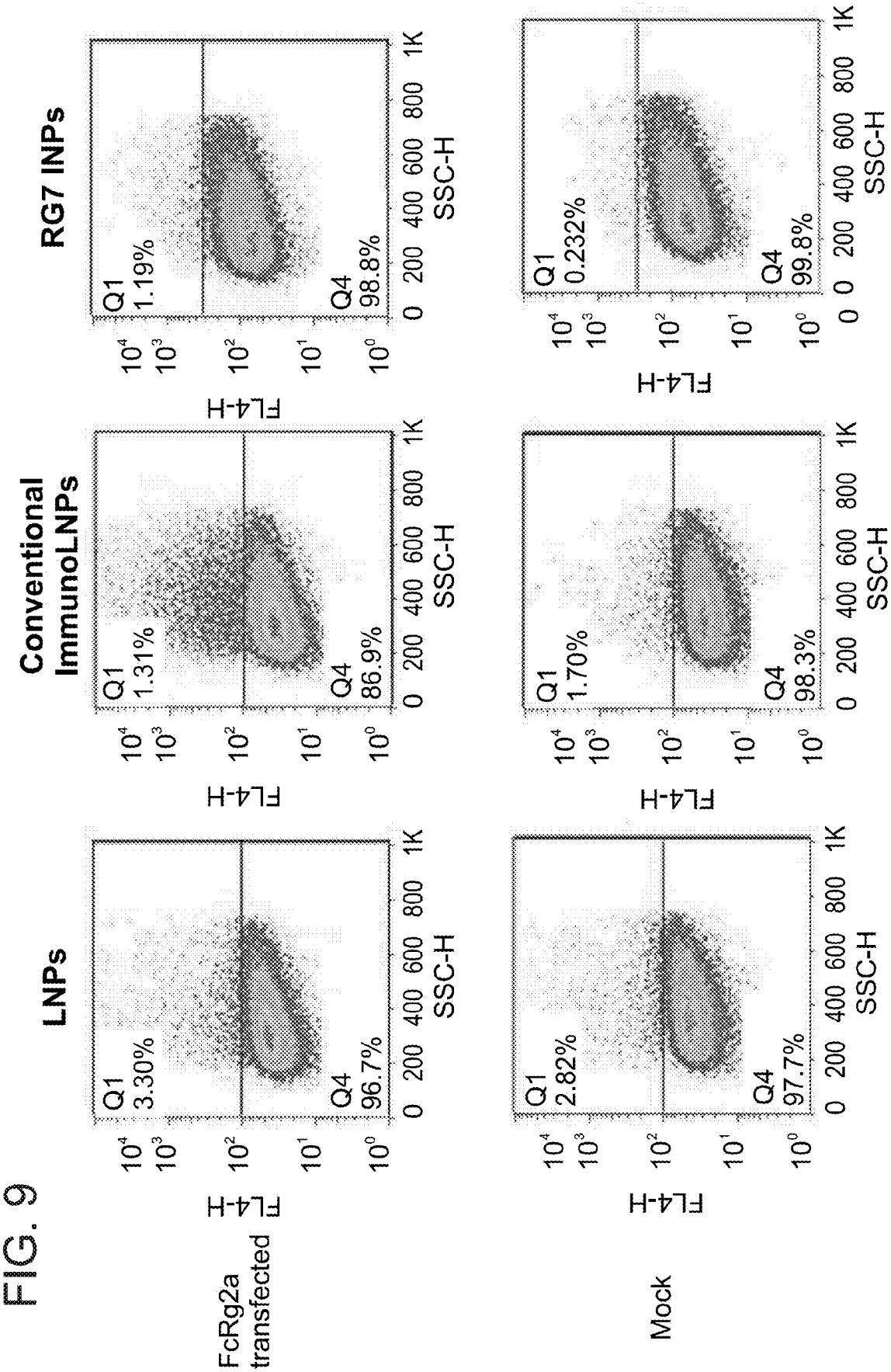

FIG. 9 are images showing that the Rg7 LNPs are able to escape FC receptor binding. To test LNPs binding to FC receptor, the 293T cell line was transfected with FcRg2a vector. Different Cy5 LNPs were tested for binding with flow cytometry: Unconjugated LNPs, LNPs conjugated to FIB504 in a conventional manner and RG7 tLNPs in a complex with FIB504.

DESCRIPTION OF SPECIFIC EMBODIMENTS OF THE INVENTION

The present invention, in some embodiments thereof, relates to immunoparticles and methods of generating and using same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

According to an aspect of the invention, there is provided a pharmaceutical composition comprising an immunoparticle which comprises a monoclonal secondary antibody immunocomplexed with a primary antibody, wherein said monoclonal secondary antibody is coupled on an outer surface of a particle and wherein said particle is loaded with a pharmaceutical agent.

As used herein the term "immunoparticles" refers to a particle which typically serves as a drug carrier to which an antibody has been coupled on a surface thereof.

As used herein, "particles" refers to nano to micro structures which are not biological cells.

The particle may be a synthetic carrier, gel or other object or material having an external surface which is capable of being loadable with (e.g., encapsulating) a pharmaceutical agent. The particle may be either polymeric or non-polymeric preparations.

Exemplary particles that may be used according to this aspect of the present invention include, but are not limited to polymeric particles, microcapsules, liposomes, microspheres, microemulsions, nanoparticles, nanocapsules, nano-spheres, nano-liposomes, nano-emulsions and nanotubes.

According to a particular embodiment, the particles are nanoparticles.

As used herein, the term "nanoparticle" refers to a particle or particles having an intermediate size between individual atoms and macroscopic bulk solids. Generally, nanoparticle has a characteristic size (e.g., diameter for generally spherical nanoparticles, or length for generally elongated nanoparticles) in the sub-micrometer range, e.g., from about 1 nm to about 500 nm, or from about 1 nm to about 200 nm, or of the order of 10 nm, e.g., from about 1 nm to about 100 nm. The nanoparticles may be of any shape, including, without limitation, elongated particle shapes, such as nanowires, or irregular shapes, in addition to more regular shapes, such as generally spherical, hexagonal and cubic nanoparticles. According to one embodiment, the nanoparticles are generally spherical.

The particles of this aspect of the present invention may have a charged surface (i.e., positively charged or negatively charged) or a neutral surface.

Agents which are used to fabricate the particles may be selected according to the desired charge required on the outer surface of the particles.

Thus, for example if a negatively charged surface is desired, the particles may be fabricated from negatively charged lipids (i.e. anionic phospholipids) such as described herein below.

When a positively charged surface is desired, the particles may be fabricated from positively charged lipids (i.e. cationic phospholipids), such as described herein below.

As mentioned, non charged particles are also contemplated by the present invention. Such particles may be fabricated from neutral lipids such as phosphatidylethanolamine or dioleilphosphatidylethanolamine (DOPE).

It will be appreciated that combinations of different lipids may be used to fabricate the particles of the present invention, including a mixture of more than one cationic lipid, a mixture of more than one anionic lipid, a mixture of more than one neutral lipid, a mixture of at least one cationic lipid and at least one anionic lipid, a mixture of at least one cationic lipid and at least one neutral lipid, a mixture of at least one anionic lipid and at least one neutral lipid and additional combinations of the above. In addition, polymer-lipid based formulations may be used.

There are numerous polymers which may be attached to lipids. Polymers typically used as lipid modifiers include, without being limited thereto: polyethylene glycol (PEG), polysialic acid, polylactic (also termed polylactide), polyglycolic acid (also termed polyglycolide), apolylactie-polyglycolic acid' polyvinyl alcohol, polyvinylpyrrolidone, polymethoxazoline, polyethyloxazoline, polyllydroxyetly-loxazolille, solyhydroxypryloxazoline, polyaspartarllide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose.

The polymers may be employed as homopolymers or as block or random copolymers.

The particles may also include other components. Examples of such other components includes, without being limited thereto, fatty alcohols, fatty acids, and/or cholesterol esters or any other pharmaceutically acceptable excipients which may affect the surface charge, the membrane fluidity and assist in the incorporation of the biologically active lipid into the lipid assembly. Examples of sterols include cholesterol, cholesterol hemisuccinate, cholesterol sulfate, or any other derivatives of cholesterol. Preferred lipid assemblies according the invention include either those which form a micelle (typically when the assembly is absent from a lipid matrix) or those which form a liposome (typically, when a lipid matrix is present).

In a specific embodiment, the particle is a liposome. As used herein and as recognized in the art, liposomes include any synthetic (i.e., not naturally occurring) structure composed of lipid bilayers, which enclose a volume. Liposomes include emulsions, foams, micelles, insoluble monolayers, liquid crystals, phospholipid dispersions, lamellar layers and the like. The liposomes may be prepared by any of the known methods in the art [Monkkonen, J. et al., 1994, J. Drug Target, 2:299-308; Monkkonen, J. et al., 1993, Calcif. Tissue Int., 53:139-145; Lasic D D., Liposomes Technology Inc., Elsevier, 1993, 63-105. (chapter 3); Winterhalter M, Lasic D D, Chem Phys Lipids, 1993 September; 64(1-3): 35-43].

The liposomes may be unilamellar or may be multilamellar. Unilamellar liposomes may be preferred in some instances as they represent a larger surface area per lipid mass. Suitable liposomes in accordance with the invention are preferably non-toxic. The liposomes may be fabricated from a single phospholipid or mixtures of phospholipids. The liposomes may also comprise other lipid materials such as cholesterol. For fabricating liposomes with a negative electrical surface potential, acidic phospho- or sphingo- or other synthetic-lipids may be used. Preferably, the lipids have a high partition coefficient into lipid bilayers and a low desorption rate from the lipid assembly. Exemplary phospholipids that may be used for fabricating liposomes with a negative electrical surface potential include, but are not limited to phosphatidylserine, phosphatidic acid, phosphatidylcholine and phosphatidyl glycerol.

Other negatively charged lipids which are not liposome forming lipids that may be used are sphingolipids such as cerebroside sulfate, and various gangliosides.

The most commonly used and commercially available lipids derivatized into lipopolymers are those based on phosphatidyl ethanolamine (PE), usually distearylphosphatidylethanolamine (DSPE).

The lipid phase of the liposome may comprise a physiologically acceptable liposome forming lipid or a combination of physiologically acceptable liposome forming lipids for medical or veterinarian applications. Liposome-forming lipids are typically those having a glycerol backbone wherein at least one of the hydrofoil groups is substituted with an acyl chain, a phosphate group, a combination or derivatives of same and may contain a chemically reactive group (such as an as amine imine, acids ester, aldelhyde or alcohol) at the headgroup. Typically, the acyl chain is between 12 to about 24 carbon atoms in length, and has varying degrees of saturation being fully, partially or non-hydrogenated lipids. Further, the lipid matrix may be of natural source, semi-synthetic or fully synthetic lipid, and neutral, negatively or positively charged.

According to one embodiment, the lipid phase comprises phospholipids.

The phospholipids may be a glycerophospholipid. Examples of glycerophospholipid include, without being limited thereto, phosphatidylglycerol (PG) including dimyristoyl phosphatidylglycerol (DMPG); phosphatidylcholine (PC), including egg yolk phosphatidylcholine and dimyristoyl phosphatidylcholine (DMPC), phosphatidic acid (PA), phosphatidylinositol (PI), phosphatidylserine (PS) and sphingomyelin (SM) and derivatives of the same.

Another group of lipid matrix employed according to the invention includes cationic lipids (monocationic or polycationic lipids). Cationic lipids typically consist of a lipophilic moiety, such as a sterol or the same glycerol backbone to which two acyl or two alkyl, or one acyl and one alkyl chain contribute the hydrophobic region of the amphipathic molecule, to form a lipid having an overall net positive charge. Preferably, the head groups of the lipid carries the positive charge. Monocationic lipids may include, for example, 1,2-dimyristoyl-3-trimethylammonium propane (DMTAP) 1,2-dioleyloxy-3-(trimethylanino) propane (DOTAP), N-[−1-(2, 3,-ditetradecyloxy)propyl]-N,N-dimethyl-N-hydroxyethylammonium bromide (DMRIE), N-[1-(2,3,-dioleyloxy)propyl]-N,N-dimethyl-N-hydroxy ethyl-ammonium bromide (DORIE), N-[1-(2,3-dioleyloxy) propyl]; —N,N,N-trimethylammonium chloride (DOTMA); 3; N—(N',N'-dimethylaminoethane) carbamoly]; cholesterol (DC-Chol), and I dimethyl-dioctadecylammonium (DDAB).

Examples of polycationic lipids include a similar lipoplilic moiety as with the mono cationic lipids, to which spermine or spermidine is attached. These include' without being limited thereto, N-[2-[[2,5-bis[3-aminopropyl)amino]-1-oxopentyl]amino]ethyl]N,N dimethul-2,3 bis (1-oXo-9-octadecenyl) oXy];-1 propanaminium (DOSPA), and ceramide carbamoyl spermine (CCS).

The cationic lipids may be used alone, in combination with cholesterol, with neutral phospholipids or other known lipid assembly components. In addition, the cationic lipids may form part of a derivatized phospholipids such as the neutral lipid dioleoylphosphatidyl ethanolamine (DOPE) derivatized with polylysine to form a cationic lipopolymer.

The diameter of the liposomes used preferably ranges from 50-200 nM and more preferably from 20-100 nM. For sizing liposomes, extrusion, homogenization or exposure to ultrasound irradiation may be used, Homogenizers which may be conveniently used include microfluidizers produced by Microfluidics of Boston, Mass. In a typical homogenization procedure, liposomes are recirculated through a standard emulsion homogenizer until selected liposomes sizes are observed. The particle size distribution can be monitored by conventional laser beam particle size discrimination. Extrusion of liposomes through a small-pore polycarbonate membrane or an asymmetric ceramic membrane is an effective method for reducing liposome sizes to a relatively well defined size distribution. Typically, the suspension is cycled through the membrane one or more times until the desired liposome size distribution is achieved. The liposomes may be extruded through successively smaller pore membranes to achieve a gradual reduction in liposome size.

According to another embodiment, the particle is a nanoparticle. Preferably, nanoparticles are less than 100 nm in diameter and can be spherical, non-spherical, or polymeric particles. In a preferred embodiment, the polymer used for fabricating nanoparticles is biocompatible and biodegradable, such as poly(DL-lactide-co-glycolide) polymer (PLGA). However, additional polymers which may be used for fabricating the nanoparticles include, but are not limited to, PLA (polylactic acid), and their copolymers, polyanhydrides, polyalkyl-cyanoacrylates (such as polyisobutylcyanoacrylate), polyethyleneglycols, polyethyleneoxides and their derivatives, chitosan, albumin, gelatin and the like.

The particles of the present invention may be modified. According modified to enhance their circulatory half-life (e.g. by PEGylation) to reduce their clearance, to prolong their scavenging time-frame and to allow antibody binding. The PEG which is incorporated into the articles may be characterized by of any of various combinations of chemical composition and/or molecular weight, depending on the application and purpose.

The term "antibody" as used in this invention includes intact molecules as well as functional fragments thereof.

As used herein, the phrase "antibody fragment" refers to a functional fragment of an antibody (such as Fab, F(ab')2, Fv, scFv, dsFv, or single domain molecules such as VH and VL) that is capable of binding to an epitope of an antigen.

Suitable antibody fragments for practicing some embodiments of the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as a Fv, a single chain Fv (scFv), a disulfide-stabilized Fv (dsFv), an Fab, an Fab', and an F(ab')2.

Functional antibody fragments comprising whole or essentially whole variable regions of both light and heavy chains are defined as follows:

(i) Fv, defined as a genetically engineered fragment consisting of the variable region of the light chain (VL) and the variable region of the heavy chain (VH) expressed as two chains;

(ii) single chain Fv ("scFv"), a genetically engineered single chain molecule including the variable region of the light chain and the variable region of the heavy chain, linked by a suitable polypeptide linker as a genetically fused single chain molecule.

(iii) disulfide-stabilized Fv ("dsFv"), a genetically engineered antibody including the variable region of the light chain and the variable region of the heavy chain, linked by a genetically engineered disulfide bond.

(iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;

(v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);

(vi) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds); and (vii) Single domain antibodies are composed of a single VH or VL domains which exhibit sufficient affinity to the antigen.

According to a specific embodiment, the secondary antibody comprises an antibody fragment. It will be appreciated that the primary antibody may also comprise an antibody fragment provided that it still comprises a conserved region to which the secondary antibody binds.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1): 86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

As used herein the term "primary antibody" refers to an antibody (or antibody fragment as defined herein) which specifically recognizes an antigenic target of interest (e.g., a protein, peptide, carbohydrate, or other small molecule) and is typically unconjugated (unlabelled). Primary antibodies that recognize and bind with high affinity and specificity to unique epitopes across a broad spectrum of biomolecules are available as high specificity (e.g., 1 μM to 0.5 nM) monoclonal antibodies and/or as polyclonal antibodies.

According to a specific embodiment, the primary or the secondary antibody is a monoclonal antibody.

According to a specific embodiment, the primary antibody comprises an antigen recognition domain which binds a tissue or tumor specific antigen.

As used herein "a tissue specific antigen" refers to a heterogenetic antigen with organ or tissue specificity.

As used herein "a tumor (or cancer) specific antigen" refers to an antigenic substance produced in tumor cells, i.e., it triggers an immune response in the host. Tumor antigens are useful in identifying tumor cells and are potential candidates for use in cancer therapy. The term also encompasses tumor associated antigens.

According to a specific embodiment, the antigen recognized by the primary antibody is a cell-surface antigen.

It will be appreciated that to improve specificity, the primary antibody refers to a plurality of primary antibodies which bind different targets e.g., 2, 3 or 4 distinct targets. Thus, one target may be a tissue specific antigen while the other(s) can be a tumor specific antigen or vise a versa. Alternatively, all the primary antibodies bind tissue specific antigens. Yet alternatively all the primary antibodies bind tumor specific antigens.

According to a specific embodiment, the primary antibody is a monoclonal antibody.

According to a specific embodiment, the primary antibody is conjugated to a pharmaceutical agent.

As used herein the phrase "secondary antibody" refers to an antibody which binds to conserved regions of a primary antibody. Thus, the secondary antibody has a specificity for the antibody species and optionally isotype of the primary antibody.

Varieties of secondary antibody are available for particular antibody classes and fragment types. Secondary antibodies can bind parts of whole IgG (heavy and light chains, H+L), or only the Fab or Fc region, or only the gamma chain. Secondary antibodies are specific for IgM heavy chains (μ or Fc5μ), or the λ or κ light chains common to all immunoglobulins (IgG, IgA, IgD, IgE and IgM).

The primary antibody and the secondary antibody can belong to any antibody class (e.g., IgG, IgA, IgD, IgE and IgM) or isotype. According to a specific embodiment, the primary antibody and the secondary are selected from the group consisting of IgG1, IgG2 and IgG4.

According to a specific embodiment, in order to improve antibody production and to reduce particle aggregation the primary antibody and the secondary antibody are of different antibody classes or antibody isotypes.

Thus according to an exemplary embodiment, the primary antibody is an IgG1 and the secondary antibody is an IgG2 or IgG4 (or vise a versa).

The secondary antibodies are typically provided as an intact antibody (e.g., whole IgG), divalent F(ab')2 fragments and monovalent Fab fragments, though other forms of antibody fragments, as described herein above can be used.

As already mentioned, the secondary antibody may be an antibody fragment which improves bioavailability since reduces depletion by Fc receptors.

Secondary antibodies are generated by immunizing a host animal with the antibody(s) from a different species. For example, anti-mouse antibodies are raised by injecting mouse antibodies into an animal other than a mouse. Goat, donkey and rabbit are the most commonly used host species for raising secondary antibodies, but others may be available as well.

The most common types of secondary antibodies are those generated against a pooled population of immunoglobulins from a target species. For example, immunizing a goat with purified mouse IgG will generate goat anti-mouse IgG antibodies that will bind to all classes, heavy and light chains (H&L) and fragments of mouse IgG as well as any other molecules sharing the same conserved domains (e.g., IgM share the same kappa light chains as IgG). In contrast, immunizing a goat with only mouse IgG1 antibodies will only generate antibodies specific for mouse IgG1 antibodies and molecules sharing the same conserved domains.

Because of the high degree of conservation in the structure of many immunoglobulin domains, class-specific secondary antibodies must be affinity purified and cross-adsorbed to achieve minimal cross-reaction with other immunoglobulins. Using the example described above, immobilized mouse IgG1 antibodies would be used to affinity purify all goat antibodies that bind to mouse IgG1. These anti-mouse IgG1 antibodies would then be further purified by passage through a chromatography column(s) containing mouse IgG2a, IgG2b, IgG3, IgM, etc., to remove any antibodies that cross-react with non-IgG1 isotypes.

Additionally, secondary antibodies can be further purified by passage through columns containing the immobilized serum proteins from species other than those used to immunize the host. This method of cross-adsorption (often referred to as "Highly Cross-Adsorbed") is an additional purification step recommended for applications where primary antibodies from multiple species will be used and when immunoglobulins or other serum proteins may be present in the samples being probed.

Since the immunoparticles of the present invention are typically used in pharmaceutical applications, they are generated non-immunogenic in the subject administered therewith.

Thus, according to a specific embodiment, the secondary antibody and optionally the primary antibody are humanized. Methods of humanizing antibodies are provided hereinabove. According to a further specific embodiment, the humanized monoclonal secondary antibody is isolated. As used herein the term "isolated" refers to retrieved from the human body and optionally further purified. Isolated can be a purified preparation which includes at least 90% antibody of interest (e.g., primary or secondary) and less than 10% other immunoglobulins.

According to a specific embodiment, the primary antibody is a human antibody (i.e., purified from human serum). In this case, for human applications, the secondary antibody is a humanized anti human secondary antibody.

The secondary antibody of the invention couples on the outer surface of the particle. Measures are taken to couple the antibody without significantly affecting its functionality in binding the primary antibody (i.e., more than 80%, 90% or 95% of the secondary antibodies on the particle are available for binding the primary antibody) and the particle's loadability or loading with the pharmaceutical agent.

Thus, the secondary antibody is coupled to the outer surface of said particle and not via the primary antibody. In such an orientation the secondary antibody is a linker for the primary antibody i.e., the secondary antibody links the primary antibody to the particle. According to a specific embodiment, the binding of the secondary antibody is not via the CDRs of the secondary antibody e.g., via the conserved regions e.g., the Fc region. Alternatively via the N terminal or the C-terminal of the secondary antibody e.g., in the case of a ScFv (see Example 5 below). The binding of the secondary antibody to the particles surface may be via a linker as further described herein.

Thus according to an aspect of the invention, there is provided a method of generating an immunoparticle, the method comprising incubating the secondary antibody (e.g., humanized or human secondary antibody) with a particle (e.g., lipid based or any other as described above) under conditions which result in an immunoparticle having coupled on an outer surface thereof a said humanized secondary antibody.

As mentioned, the conditions for the coupling are selected to result in directional coupling of the secondary antibody to the outer surface of the particle, such that the secondary antibody maintains its functionality following the binding.

Methods of coupling antibodies on particle's outer surface (e.g., liposomes) are known in the art.

As used herein "coupling" or "coupled on" refers to covalent or non-covalent attachment of the antibody to the particle.

Antibody conjugation methods which can be used in accordance with the teachings of the present invention can be divided to direct binding or indirect binding. Some methods are provided hereinbelow and are summarized in Ansell, Supra. While specifically referring to liposomes, the procedures described hereinbelow may be applied to a variety of particles, while using modified protocols simply applied by the ordinary artisan.

Direct conjugation methods are well known to those of skill in the art. See for example, G. Gregoriadis, (1984) "Liposome Technology" CRC Press, Boca Raton, Fla. and D. D. Lasic, "Liposomes: from physics to applications" (1993) Elsevier, Amsterdam; N.Y. Particularly preferred is conjugation through a thioether linkage. This may be accomplished by reacting the antibody with a maleimide derivatized lipid such as maleimide derivatized phosphatidylethanolamine (M-PE) or dipalmitoylethanolamine (M-DEP). This approach is described in detail by Martin et al. J. Biol. Chem., 257: 286-288 (1982) which is incorporated herein by reference.

In another preferred embodiment, the antibody can be coupled to a hydrophilic polymer (e.g., a PEG). Means of attaching targeting molecules to polymer linkers are well known to those of skill in the art (see, e.g., chapter 4 in Monoclonal Antibodies: Principles and Applications, Birch and Lennox, eds., John Wiley & Sons, Inc., New York (1995); and Blume et al. Biochem. Biophys. Acta. 1149: 180-184 (1993). In a particularly preferred embodiment, an antibody or a fragment thereof (e.g., Fab' fragment) is linked to a maleimide derivatized PEG through the —SH group of the antibody. To provide a linker group, alpha-distearoylphosphatid-ylethanolaminocarbonyl-psi-malimidopropionylamidopolyethylene glycol is synthesized from distearoylphosphatidylethanolamine and heterobifunctional PEG derivative, N-hydroxysuccinimidyl-PEG-maleimide according to standard methods. The maleimide-derivative of PEG-PE is included in the liposome preparation as described above and below and the antibody can be conjugated with the liposome via the sulfhydryl group at pH 7.2.

Amine modifications making use of cross-linking agents such as EDC are taught in Endoh et al. 1981 J. Immun. Meth. 44:79-85; Dunnick 1975 J. Nuclear. Med. 16:483-487; Alternatively, direct modification of antibodies with activated fatty acids, such as N-hydroxysuccinimide (NHS) eater or palmitic acid, prior to incorporation into a liposome membrane, typically by detergent dialysis procedures (Huang et al. 1980, J. Biol. Chem. 255:8015-8018. Reagents, such as EDC, are used in conjunction with NHS to activate acidic functions on liposomes, which are then conjugated to the amino groups on antibodies. Better control of the conjugation reaction can be achieved using heterobifunctional cross-linkers which efficiently introduce a unique and selective reactive function, such as a protected thiol or maleimide group. Examples of these crosslinkers are SPDP (Barbet et al. 1981 J. Supramolec. Struct. Cell. Biochem. 16:243-258), S-acetylthioglycolic acid N-hydroxysuccinimide ester (SATA, Jones 1993 Biochim. Biophys. Acta. 1152: 23:1-32; Schwendener 1990 Biochim. Biophys. Acta. 1026: 69-79 and 4-(p-maleimidophenyl)butyric acid N-hydroxysuccinimide ester (SMPB (Hansen 1995 Biochim. Biophys. Acta. 1239:133-144). Antibodies which have been activated by these crosslinkers can, after deprotection where appropriate, react with activated lipids in liposome bilayers. Maleimide and protected thiol-derivatized lipids are available from commercial sources for this purpose.

Deprotection of 3-pyridyl disulfides is usually effected by DTT and occasionally by some other mercaptan. Once deprotected, sulfhydryl groups can react with maleimide (for example SMPB-modified conjugates) or iodo (for example, iodoacetic acid N-hydroxysuccinimide ester (SIAA)-modified conjugates) groups. Maleimide groups are recommended since iodo functions can react with amino groups in either of the substrates, leading to undesirable side products. Deprotection is not required for these reagents.

Indirect Conjugation Methods

Biotin-avidin—For example, a biotin conjugated secondary antibody may be bound to a particle (e.g., liposome) containing a streptavidin. Alternatively, the biotinylated antibody may be conjugated to a biotin derivatized liposome by an avidin or streptavidin linker. Ahmad et al., Cancer Res., 52: 4817-4820 (1992) which is herein incorporated by reference, describes such a mode of coupling. When monovalent Fab molecules are used, typically about 30 to 125 and more typically about 50 to 100 Fab' molecules per liposome are used.

Binding via protein A/G/L-liposome conjugates targeted to the Fc chain of antibodies is taught in Matthay et al. 1986 Cancer Res. 46:4904-4910; Machy et al. 1983 Biochem. Biophys. Acta. 901:157-160.

It will be appreciated that one an immunoparticles is generated it may be packed in a container and identified as a universal kit for in-vivo delivery of a pharmaceutical agent. The kit may further comprise instructions for performing immunocomplexation of the immunoparticles with the primary antibody.

Loading of the particle with the pharmaceutical agent can be effected concomitant with, or following particle assembly.

Thus, in one preferred embodiment, for example, when the pharmaceutical agent is a nucleic acid, e.g., DNA, RNA, siRNA, plasmid DNA, short-hairpin RNA, small temporal RNA (stRNA), microRNA (miRNA), RNA mimetics, or heterochromatic siRNA, the nucleic acid agent of interest has a charged backbone that prevents efficient encapsulation in the lipid particle. Accordingly, the nucleic acid agent of interest may be condensed with a cationic polymer, e.g., PEI, polyamine spermidine, and spermine, or cationic peptide, e.g., protamine and polylysine, prior to encapsulation in the lipid particle. In one embodiment, the agent is not condensed with a cationic polymer.

In another embodiment, the agent of interest is encapsulated in the lipid particle in the following manner. The immunoparticle is provided lyophilized. The agent of interest is in an aqueous solution. The agent of interest in aqueous solution is utilized to rehydrate the lyophilized lipid particle. Thus, the agent of interest is encapsulated in the rehydrated lipid particle.

In one embodiment, two agents of interest may be delivered by the immunoparticles (e.g., lipid based particle). One agent is hydrophobic and the other is hydrophilic. The hydrophobic agent may be added to the lipid particle during formation of the lipid particle. The hydrophobic agent associates with the lipid portion of the lipid particle. The hydrophilic agent is added in the aqueous solution rehydrating the lyophilized lipid particle. In an exemplary embodiment of two agent delivery a condensed siRNA is encapsulated in a liposome and wherein a drug that is poorly soluble in aqueous solution is associated with the lipid portion of the lipid particle. As used herein, "poorly soluble in aqueous solution" refers to a composition that is less that 10% soluble in water.

Any suitable lipid: pharmaceutical agent ratio that is efficacious is contemplated by this invention. Preferred lipid: pharmaceutical agent molar ratios include about 2:1 to about 30:1, about 5:1 to about 100:1, about 10:1 to about 40:1, about 15:1 to about 25:1.

The preferred loading efficiency of pharmaceutical agent is a percent encapsulated pharmaceutical agent of about 50%, about 60%, about 70% or greater. In one embodiment, the loading efficiency for a hydrophilic agent is a range from 50-100%. The preferred loading efficiency of pharmaceutical agent associated with the lipid portion of the lipid particle, e.g., a pharmaceutical agent poorly soluble in aqueous solution, is a percent loaded pharmaceutical agent of about 50%, about 60%, about 70%, about 80%, about 90%, about 100%. In one embodiment, the loading efficiency for a hydrophobic agent in the lipid layer is a range from 80-100%.

As used herein "loading" refers to encapsulating or absorbing.

The term "encapsulated" as used herein refers to the pharmaceutical agent being distributed in the interior portion of the particles. Preferably, the pharmaceutical agents are homogenously distributed. Homogeneous distribution of a pharmaceutical agent in polymer particles is known as a matrix encapsulation. However, due to the manufacturing process it is foreseen that minor amounts of the pharmaceutical agent may also be present on the outside of the particle and/or mixed with the polymer making up the shell of the particle.

As used herein "absorbed" refers to binding of the pharmaceutical agent to the outer surface of the particle.

According to a specific embodiment, immunocomplexation of the primary antibody with the secondary antibody, refers to antibody (i.e., secondary antibody)-antigen (i.e., primary antibody)-based interaction. Antibody-antigen binding is a non-covalent, reversible interaction (specific binding is typically in the 1 µM-1 nM range), which fully maintains the functionality of the primary antibody in binding its epitope. According to a specific embodiment, the immunocomplexation reaction is effected ex-vivo.

Conditions for performing immunocomplexation are well known in the art and require physiological conditions and avoid high salt concentrations and extremes of pH which disrupt antigen-antibody binding by weakening electrostatic interactions and/or hydrogen bonds.

The particles of the present invention may be administered to the subject per se or as part of a pharmaceutical composition. As used herein a "pharmaceutical composition" refers to a preparation of the particles encapsulating the active ingredients described herein with other chemical components such as physiologically suitable carriers and excipients.

According to a specific embodiment, the pharmaceutical composition comprises an immunoparticle comprising a monoclonal secondary antibody (e.g., humanized) immunocomplexed with a primary antibody, wherein said monoclonal secondary antibody is coupled on an outer surface of a particle and wherein said particle is loaded with a pharmaceutical agent.

According to a specific embodiment, the pharmaceutical agent is a therapeutic agent.

Exemplary therapeutic agents include nucleic acid, polynucleotide, gene, and analogs thereof; anticancer agent (e.g., chemotherapy, radioisotopes, immunotherapy), antibiotic, enzyme, antioxidant, lipid intake inhibitor, hormone, anti-inflammatory, steroid, vasodilator, angiotensin converting enzyme inhibitor, angiotensin receptor antagonist, inhibitor for smooth muscle cell growth and migration, platelet aggregation inhibitor, anticoagulant, inhibitor for release of chemical mediator, promoter or inhibitor for endothelial cell growth, aldose reductase inhibitor, inhibitor for mesangium cell growth, lipoxygenase inhibitor, immunosuppressive, immunostimulant, antiviral agent, Maillard reaction suppressor, amyloidosis inhibitor, nitric oxide synthetic inhibitor, AGEs (Advanced glycation endproducts) inhibitor, radical scavenger, protein, peptide; glycosaminoglycan and derivatives thereof; and oligosaccharide, polysaccharide, and derivatives thereof.

According to a specific embodiment, the pharmaceutical agent is a diagnostic agent.

Exemplary diagnostic drugs include in vivo diagnostics such as an X ray contrast medium, a diagnostic agent for ultrasound, an isotope-labeled agent for diagnosis by nuclear medicine, and an agent for diagnosis by nuclear magnetic resonance.

The desired amount of the drug loaded in the particle varies depending on the type of the drug. However, it is preferable that the drug can be loaded in the particle at a high loading efficiency.

According to another specific embodiment, the pharmaceutical composition comprises the humanized secondary antibody.

The purpose of the pharmaceutical composition is to facilitate administration of the active ingredients to the subject.

Herein the term "active ingredient" refers to the pharmaceutical agents.

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered active ingredients. An adjuvant is included under these phrases.

Herein, the term "excipient" refers to an inert substance added to the pharmaceutical composition to further facilitate administration of an active ingredient of the present invention. Examples, without limitation, of excipients include calcium carbonate, calcium phosphate, various sugars and types of starch, cellulose derivatives, gelatin, vegetable oils and polyethylene glycols. The pharmaceutical composition may advantageously take the form of a foam or a gel.

Techniques for formulation and administration of drugs may be found in "Remington's Pharmaceutical Sciences," Mack Publishing Co., Easton, Pa., latest edition, which is incorporated herein by reference.

Suitable routes of administration include any of various suitable systemic and/or local routes of administration.

Suitable routes of administration may, for example, include the inhalation, oral, buccal, rectal, transmucosal, topical, transdermal, intradermal, transnasal, intestinal and/or parenteral routes; the intramuscular, subcutaneous and/or intramedullary injection routes; the intrathecal, direct intraventricular, intravenous, intraperitoneal, intranasal, and/or intraocular injection routes.

The pharmaceutical composition may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

For transmucosal administration, penetrants appropriate to the barrier to be permeated are used in the formulation. Such penetrants are generally known in the art.

For oral administration, the pharmaceutical composition can be formulated readily by combining the active ingredients with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration via the inhalation route, the active ingredients for use according to the present invention can be delivered in the form of an aerosol/spray presentation from a pressurized pack or a nebulizer with the use of a suitable propellant, e.g., a fluorochlorohydrocarbon such as dichlorodifluoromethane, trichlorofluoromethane, dichloro-tetrafluoroethane; carbon dioxide; or a volatile hydrocarbon such as butane, propane, isobutane, or mixtures thereof. In the case of a pressurized aerosol, the dosage unit may be determined by providing a valve to deliver a metered amount. Capsules and cartridges of, e.g., gelatin for use in a dispenser may be formulated containing a powder mix of the active ingredients and a suitable powder base such as lactose or starch.

The pharmaceutical composition may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

A pharmaceutical composition for parenteral administration may include an aqueous solution of the active ingredients in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredients may be in powder form for constitution with a suitable vehicle, e.g., sterile, pyrogen-free water based solution, before use.

The pharmaceutical composition may also be formulated in rectal compositions such as suppositories or retention enemas, using, e.g., conventional suppository bases such as cocoa butter or other glycerides.

The pharmaceutical composition should contain the active ingredients in an amount effective to achieve disease treatment.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays—e.g. lysosomal enzyme comprising particles may be tested for in-vitro activity in plasma or in other plasma mimicking environments. For example, a dose can be formulated in animal models (e.g. Fabry mice which comprise high levels of globotriaosylceramide) to achieve a desired tissue concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or tissue levels of the active ingredients which are sufficient to achieve the desired therapeutic effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of the composition to be administered will be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredients. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

The immunoparticles of the present invention may be used to deliver a pharmaceutical agent to a subject in need thereof. Both therapeutic and clinical applications are contemplated herein.

Subjects who may be treated according to the methods described herein are typically mammalian subjects, e.g. human.

The present teachings can be used in a variety of clinical applications which will benefit from the implementation of such a simple and cost-effective platform.

It is expected that during the life of a patent maturing from this application many relevant particles will be developed and the scope of the term immunoparticle is intended to include all such new technologies a priori.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990);

Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Materials

Soy phosphatidylcholine (PC), Cholesterol (Chol) and 1,2-distearoyl-sn-glycero-3-phosphoethanolamine-N-[carboxy(polyethylene glycol)-2000] (DS PE-PEG(2000)-COOH) were purchased from Avanti Polar lipids Inc. (Alabaster, Ala., USA). Dextran FITC 10 Kd was purchased from sigma-aldrich (Rehovot, Israel). 1-(3-dimethylaminopropyl)-3-ethylcarbodimidehydrochloride (EDC) was purchased from sigma-aldrich (Rehovot, Israel) and sulfo-hydroxysuccinimide (sulfo-NHS) was purchased from ProteoChem (Denver, USA).

Nanoparticles (NPs) Preparation

NPs were prepared as previously described, without surface modification[5] and [6]. Briefly, Multilamellar NPs (MLV), composed of PC, chol and DSPE-PEG(2000)-COOH at molar ratios of 30:9:1 respectively, were prepared by a lipid-film method and evaporated to dryness using a buchi-rotovap. The lipid film was hydrated with 3 mg/ml FITC dextran (MW10K) in Phosphate-buffered saline pH 7.4 to create MLV. Resulting MLV were extruded into small unilamellar nano-scale vesicles (ULV) with a Thermobarrel Lipex Extruder™ (Lipex biomembranes Inc., Vancouver, British Columbia, Canada) at 60° C. under nitrogen pressures of 300-550 psi. The extrusion was carried out in a stepwise manner using progressively decreasing pore-sized membranes (from 1, 0.8, 0.6, 0.4, 0.2, to 0.1 um) (Nucleopore, Whatman), with 10 cycles per pore-size. Free FITC dextran was removed using a size exclusion column packed with sepharose CL-4B beads (CL-4B column), equilibrated with PBS. Particle diameters and surface charges (zeta potential) were measured using a Malvern Zetasizer nano ZSo (Malvern Instruments Ltd., Southborough, Mass.).

Secondary LNPs Conjugation

FITC dextran PEG NPs were coupled to RG7 mAbs using an amine-coupling method. Briefly, 180 μL NPs in 20 mM MES buffer PH5.5 were incubated with 10 μL of 1M EDC and 10 μL of 1M sulfo-NHS for 10 minutes at room temperature with gentle stirring. Free cross linkers were removed using CL-4B column, equilibrated with PBS. The resulting NHS activated NPs were mixed with 200 ug RG7 and incubated for 150 min at room temperature with gentle stirring following incubation overnight at 4° C. To remove free antibody an ultracentrifuge was used (100000G, 40 min) following CL-4B column.

Cell Culture, Primary Splenocytes and Keratinocytes Isolation

Primary keratinocytes were isolated as follow: a scalpel was used to remove fat and underlying subcutis from the back skins of adult C57BL/6 mice, and following trypsinization, neutralized cell suspensions were strained (70 μM, then 40 μM pores; BD Biosciences). Single cell suspensions in 2% FCS in PBS were then taken to NPs binding assay.

Primary splenocytes were isolated from C57BL/6 spleen as was previously described [5]. Tk1 cell line was grown in RPMI with 10% fetal calf serum. 3T3NIH cell line was grown in DMEM supplemented with 10% fetal calf serum.

Flow Cytometry and NPs Binding Assay $0.5*10^6$ cells were used. Cells were incubated with anti-mouse CD34 (clone mec14.7, hair follicle stem cells and fibroblasts, Biolegend) or anti-mouse integrin beta 7 (clone FIB504, Tk1 cells, bio X cell) or anti-mouse CD3ε (clone: KT3, T cells, AbD serotec). Antibodies diluted in PBS with 1% FCS and stained for 30 min at 4° C. Cells were washed with PBS following incubation with anti Rat IgG2a FC monoclonal antibody (clone RG7/1.3, ATCC) (RG7) or secondary LNPs. Antibodies or liposomes were diluted in PBS with 1% FCS and stained for 30 min at 4° C. Cells were washed with PBS. In some experiments the cells were incubated with PE-conjugated F(ab')2 Donkey anti-mouse IgG(H+L) (minimal cross-reaction to Rat) (Jackson) to detect RG7 or secondary LNPs or with PE-conjugated F(ab')2 Donkey anti-Rat IgG(H+L) (minimal cross-reaction to Rat) (Jackson, catalog number 712-116-153) to detect the primary antibody (anti CD34, anti-integrin beta 7 or anti CD3). In the splenocytes experiment, secondary LNPs were detected in the FL1 channel by FITC dextran and further staining was performed with anti-mouse CD11b-PE (clone M1/70—expressed on granulocytes, monocytes, macrophages, myeloid-derived dendritic cells, and natural killer cells), anti-mouse CD4-PE (clone GK1.5, T cells, Biolegend) and anti-mouse CD19 (clone 6D5, Biolegend). In the primary keratinocytes experiment, 7AAD was added to stain dead cells that were gated out in the analysis. Data were acquired and analyzed on FACScan or FACScalibur with CellQuest software (Becton Dickinson, Franklin Lakes, N.J.).

Example 2

Secondary Antibody Qualification

Rg7/1.3 binds rat IgG2a Antibodies in Three Different Cell Lines

Rg7/1.30 (RG7) clone [4] is a monoclonal antibody against rat $IgG_{2a}$ (Fc). The present inventors have verified RG7 functionality in a flow cytometry assay in which RG7 was incubated with cell line that was bound to rat $IgG_{2a}$ primary antibody. FIG. 1A shows that RG7 binds 3T3 cell line only in the presence of anti CD34 antibody. Binding of RG7 to TK1 cell line is demonstrated in FIG. 1B, where RG7 was bound to the cells only in the presence of FIB504.64 antibody.

Example 2

Secondary LNPs Construction

Having validated RG7 functionality, the present inventors used it to form secondary LNPs that will serve as a universal targeted delivery platform (FIG. 2).

To construct secondary LNPs, PEG—decorated nanoscaled NPs encapsulating FITC—dextran (10K MW) were prepared, as a drug model. Particle diameters was 124.8 (±0.56) nm and surface charges (zeta potential) was −31.8 (±1.6) mV. To construct secondary LNPs, pegylated NPs were coupled to RG7 mAb using EDAC and sulfo-NHS coupling agents (FIG. 1A AND 1B). Uncongujated, free RG7 mAb, was removed by ultracentrifuge (400,000 G, 40 min) following CL-4B column purification.

To test secondary LNPs functionality, the present inventors have examined NPs binding to TK1 cell line in the presence or absence of the FIB504.64 (Rat IgG$_{2a}$ antibody, that binds to Integrin β$_7$ expressed on these cells). Secondary LNPs were detected both in the FL-1 channel, due to their florescence character and in the FL-2 channel, using secondary anti mouse PE antibody (excluded to Rat), which recognize the RG7 antibody.

As shown in FIGS. 3A-3B only in the presence of FIB504.64, secondary LNPs were bound to TK1 cell line.

To further examine the specific binding of secondary LNPs, the present inventors have tested their specific binding in a heterogeneous cell population. TK1 cells were co-cultured with NIH3T3 cells and were subjected to secondary LNPs with or without FIB504.64 that do not bind NIH3T3 cell line. FIG. 4A demonstrates the specific binding of secondary LNPs to TK1 cells, which are detected using their SSC profile, which is much smaller than the NIH3T3 cell line. The specific binding took place only in the presence of FIB504.64. FIG. 4B present specific binding of secondary LNPs to T cells in primary splenocytes population, using anti CD3 (Rat IgG$_{2a}$) as prime antibody and FIG. 4C shows targeted binding of secondary LNPs to hair follicle stem cells in primary keratinocytes population, using anti CD34 (Rat IgG$_{2a}$).

Example 3

Secondary LNPs—Primary Antibody Complex Formation

To target certain cell type in-vivo, secondary LNPs—primary antibody complex should be maintained. To establish the complex, secondary LNPs were incubated with FIB504.64 for 2 hours at RT or PBS buffer, as a control. After ultracentrifuge and CL-4B column purification, secondary LNPs and FIB504.64-secondary LNPs complex was incubated with TK1 cells. Secondary LNPs were detected in the FL1 channel due to the presence of FITC dextran encapsulated in the NPs, as well as with channel 2, using secondary mouse PE (Rat excluded). The presence of FIB504.64 was also detected using secondary Rat PE (mouse excluded). The complex binding was compared to secondary LNPs binding to TK1 cells as a negative control, as well as to secondary LNPs binding to TK1 cells, which have been previously bound to FIB504.64 as a positive control. As shown in FIGS. 5A-5C the complex has been formed and it binds Tk1 cells. The binding as a complex is highly specific.

Example 4

Secondary LNPs—Primary Antibody Complex In-Vivo

To examine the feasibility of the Secondary LNPs to target specific cell population in-vivo, a complex of secondary LNPs with a primary antibody against CD3, a T cells marker, was generated. Specific targeting of the complex was validated ex-vivo on splenocytes (data not shown). To examine the ability to target cells in-vivo, the present inventors have injected the complex (20 mg/Kg body) I.V and isolated splenocytes after an hour. Cy5 labeled Secondary LNPs were detected at the FL4 channel. As shown in FIGS. 6A-6C, analysis of cells population (Th cells, B cells and monocytes) demonstrated that the immunoliposome (i.e., the complex) targeted specifically the T cell population.

Example 5

An scFv Fragment as a Secondary Linker Platform

In order to examine the possibility of using a derivative of a secondary monoclonal antibody as a linker, an scFv was constructed from the RG7/1.3 hybridoma cell line. The scFv was expressed in *E. coli* and purified using His Trap column. RG7 scFv binding to Rat IgG$_{2a}$ was measured with ELISA, whereby Rat IgG2a Isotype antibody, or BSA as a control, served for coating.

FIG. 7A presents high affinity of the scFv with estimated Kd of ~10 nM. FIG. 7B shows the ability of the scFv to bind Tk1 cells that were pre-incubated with FIB504 (Rat IgG$_{2a}$ antibody). Detection of the scFv was carried out using anti His antibody.

To construct LNPs scFv, several lysine residues were added upstream to the scFv. Using EDC NHS linkers the present inventors have conjugated the scFv to the LNPs. The ability of the LNPs scFv to form a complex was examined by incubating the scFv LNPs with florescent Rat IgG$_{2a}$. After column purification the LNPs fluorescence was determined by flow cytometry. FIG. 7C presents the ability of the particles to bind FITC Rat IgG$_{2a}$ or PE Rat IgG$_{2a}$ antibodies and to form a complex. To test scFv LNPs ability to target cells in-vivo, Cy5 scFv LNPs were incubated with anti CD4 and injected I.V to V57/b16 mice. Following 1 hour splenocytes were isolated and targeting was examined by flow cytometry. As shown in FIG. 7D, CD4 scFv LNPs target specifically the CD4 cell population. Confocal images also present internalization of the LNPs into the cells.

Example 6

Tri-Specific Targeting

The universal platform enables also binding to several primary antibodies. To test the possible advantages of such a system RG7 LNPs were prepared with one or more primary antibodies and their affinity to Tk1 cell line was examined. Antibodies against different receptors expressed on those cells were examined such as Integrin beta 7, CD3 and LFA-1. FIG. 8 clearly demonstrates the advantage of using several primary antibodies rather than one, since more LNPs were bound to the cells using the combination of the three primary antibodies. This indicates a higher affinity of the tri-specific LNPs to the cells. These results open interesting possibilities for targeting.

Example 7

The Secondary tINP Platform Improves the Bioavailability of the Particles

One major LNPs clearance pathway involves recognition of the immunoLNPs by the FC receptor, expressed on immune cells, such as monocytes. It was therefore hypothesized that since in the present platform the Fc portion is not oriented towards the cells, unlike conventional LNPs, where the antibody orientation is random, the binding to Fc receptors will be reduced thereby reducing LNPs clearance.

To examine this question the present inventors have expressed CD32a (Rat FcRg2a) on 293T cell line and examined the binding of several LNPs. LNPs, conventional LNPs and RG7 LNPs. FIG. 9 demonstrates the binding of conventional LNPs only to FcRg2a transfected cells. Although transfection percent is low (13%, data not shown), it is clear that RG7 LNPs has a great advantage over conventional LNPs. It is important to mention that both conventional LNPs (with FIB504 Ab) and RG7 LNPs in a complex with FIB504 were tested for functionality on Tk1 cell line (data not shown).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of delivering a pharmaceutical agent to a subject in need thereof, the method comprising administering to the subject an immunoparticle comprising a humanized secondary antibody coupled on an outer surface of a particle, wherein said secondary antibody is bound specifically to an Fc region of an isolated humanized or human primary antibody and wherein said immunoparticle is loaded with the pharmaceutical agent, thereby delivering the pharmaceutical agent to the subject.

2. The method of claim 1, wherein said administering is systemically administering.

3. The method of claim 1, wherein said isolated humanized secondary antibody is an IgG.

4. The method of claim 1, wherein said humanized or human primary antibody is IgG1.

5. The method of claim 1, wherein said primary antibody comprises an antigen recognition region which binds a tissue specific antigen.

6. The method of claim 1, wherein said primary antibody comprises an antigen recognition region which binds a cancer specific antigen.

7. The method of claim 1, wherein said particle is selected from the group consisting of a polymeric particle, a microcapsule, a liposome, a microsphere, a microemulsion, a nanoparticle, a nanocapsule, a nanosphere and a nanocage.

8. The method of claim 1, wherein said particle comprises a charged external surface.

9. The method of claim 1, wherein said particle comprises a neutral external surface.

10. The method of claim 1, wherein said particle is lipid-based particle.

11. The method of claim 1, wherein said subject is a human subject.

* * * * *